(12) United States Patent
Metcalfe et al.

(10) Patent No.: US 6,803,046 B2
(45) Date of Patent: Oct. 12, 2004

(54) SINCALIDE FORMULATIONS

(75) Inventors: Edmund C. Metcalfe, Hillsborough, NJ (US); Jo Anna Monteferrante, Raritan Township, NJ (US); Margaret Newborn, Hamilton Township, NJ (US); Irene Ropiak, Lawrenceville, NJ (US); Ernst Schramm, North Brunswick, NJ (US); Gregory W. White, Monmouth Junction, NJ (US); Julius P. Zodda, Mercerville, NJ (US)

(73) Assignee: Bracco International B.V., Amsterdam (NL)

( * ) Notice: Subject to any disclaimer, the term of this patent is extended or adjusted under 35 U.S.C. 154(b) by 0 days.

(21) Appl. No.: 10/222,540

(22) Filed: Aug. 16, 2002

(65) Prior Publication Data

US 2004/0033243 A1 Feb. 19, 2004

(51) Int. Cl.[7] .................................................. A61K 9/00

(52) U.S. Cl. ........................ 424/400; 514/1.65; 514/18; 514/19; 514/951

(58) Field of Search .......................... 424/400; 514/18, 514/19, 1.65, 951

(56) References Cited

U.S. PATENT DOCUMENTS

| | | | |
|---|---|---|---|
| 3,723,406 A | 3/1973 | Ondetti et al. ........... | 260/112.5 |
| 5,011,678 A | * 4/1991 | Wang et al. .................. | 424/45 |
| 5,555,610 A | 9/1996 | Yan et al. ................... | 424/9.52 |
| 5,567,414 A | 10/1996 | Schneider et al. .......... | 424/9.52 |
| 5,833,948 A | 11/1998 | Tournier et al. .......... | 424/9.321 |
| 6,110,443 A | 8/2000 | Schneider et al. ......... | 424/9.51 |
| 6,306,905 B1 | 10/2001 | Kurz et al. .................. | 514/551 |
| 6,326,406 B1 | 12/2001 | De Tommaso ............... | 514/731 |
| 6,358,528 B1 | 3/2002 | Grimmett et al. ........... | 424/474 |

OTHER PUBLICATIONS

Sitzmann, et al., "Cholecystokinin Prevents Parenteral Nutrition Induced Biliary Sludge in Humans," Surgery, Gynecology & Obstetrics, vol. 170, Jan. 1990, pp. 25–31.

Teitelbaum et al., "Treatment of Parenteral Nutrition–Associated Cholestasis with Cholecystokinin–Octapeptide," Journal of Pediatric Surgery, vol. 30, No. 7, Jul. 1995, pp. 1082–1085.

Moss and Amii, "New Approaches to Understanding the Etiology and Treatment of Total Parenteral Nutrition–Associated Cholestasis," Seminars in Pediatric Surgery, vol. 8, No. 3, Aug. 1999, pp. 140–147.

Teitelbaum, "Parenteral Nutrition–Associated Cholestasis," Current Opinion in Pediatrics, vol. 9, 1997, pp. 270–275.

Teitelbaum and Tracy, "Parenteral Nutrition–Associated Cholestasis," Seminars in Pediatric Surgery, vol. 10, No. 2, May 2001, pp. 72–80.

Strickley, "Parenteral Formulations of Small Molecules Therapeutics Marketed in the United States (1999) —Part 1," PDA Journal of Pharmaceutical Science & Technology, vol. 53, No. 6, Nov.–Dec. 1999, pp. 324–349.

Strickley, "Parenteral Formulations of Small Molecules Therapeutics Marketed in the United States (1999)—Part II," PDA Journal of Pharmaceutical Science & Technology, vol. 54, No. 1, Jan.–Feb. 2000, pp. 69–96.

(List continued on next page.)

*Primary Examiner*—Thurman K. Page
*Assistant Examiner*—Konata M. George
(74) *Attorney, Agent, or Firm*—Kramer, Levin, Naftalis & Frankel LLP

(57) ABSTRACT

The invention features sincalide formulations that include an effective amount of sincalide, a bulking agent/tonicity adjuster, a stabilizer, a surfactant, a chelator, and a buffer. The invention also features kits and methods for preparing improved sincalide formulations, as well as methods for treating, preventing, and diagnosing gall bladder-related disorders using sincalide formulations.

108 Claims, 12 Drawing Sheets

OTHER PUBLICATIONS

Strickley, "Parenteral Formulations of Small Molecules Therapeutics Marketed in the United States (1999)—Part III," PDA Journal of Pharmaceutical Science & Technology, vol. 54, No. 2, Mar.–Apr. 2000, pp. 152–169.

Nema et al., "Excipients and Their Use in Injectable Products," PDA Journal of Pharmaceutical Science & Technology, vol. 51, No. 4, Jul.–Aug. 1997, pp. 166–171.

Wang and Hanson "Parenteral Formulations of Proteins and Peptides: Stability and Stabilizers, " Journal of Parenteral Science & Technology, vol. 42, Supplement 1988, pp. S3–S25.

Carpenter et al., "Freezing–and Drying–Induced Perturbations of Protein Structure and Mechanisms of Protein Protection by Stabilizing Addditives," Drugs and the Pharmaceutical Sciences, vol. 96, 1999, pp. 123–160.

Pikal, "Mechanisms of Protein Stabilization During Freeze–Drying and Storage: The Relative Importance of Thermodynamic Stabilization and Glassy State Relaxation Dynamics," Drugs and the Pharmaceutical Sciences, vol. 96, 1999, pp. 161–197.

Shah et al., "The Effects of Various Excipients on the Unfolding of Basic Fibroblast Growth Factor," PDA Journal of Pharmaceutical Science & Technology, vol. 52, No. 5, Sep.–Oct. 1998, pp. 209–214.

Powell et al., "Compendium of Excipients for Parenteral Formulations," PDA Journal of Pharmaceutical Science & Technology, vol. 52, No. 5, Sep.–Oct. 1998, pp. 238–311.

Zeissman, "Cholecystokinin Cholescintigraphy: Victim of Its Own Success?" Journal of Nuclear Medicine, vol. 40, No. 12, Dec. 1999, pp. 2038–2042.

Krishnamurthy and Krishnamurthy, "Gallbladder Ejection Fraction: A Decade of Progress and Future Promise," Journal of Nuclear Medicine, vol. 32, No. 4, Apr. 1992, pp. 542–544.

Krishnamurthy et al., "Quantitative Biliary Dynamics: Introduction of a New Noninvasive Scintigraphic Technique," Journal of Nuclear Medicine, vol. 24, No. 3, 1983, pp. 217–223.

Mesgarzadeh et al., "Filling, Postcholecystokinin Emptying, and Refilling of Normal Gallbladder: Effects of Two Different Doses of CCK on Refilling: Concise Communication," Journal of Nuclear Medicine, vol. 24, No. 8, 1983, pp. 666–671.

Krishnamurthy et al., "The Gallbladder Emptying Response to Sequential Exogenous and Endogenous Cholecystokinin," Nuclear Medicine Communications, vol. 5, 1984, pp. 27–33.

Krishnamurthy et al., "Detection, Localization, and Quantitation of Degree of Common Bile Duct Obstruction by Scintigraphy," Journal of Nuclear Medicine, vol. 26, No. 7, Jul. 1985, pp. 726–735.

Fink–Bennett et al., "Cholecystokinin Cholescintigraphic Findings in the Cystic Duct Syndrome," Journal of Nuclear Medicine, vol. 26, No. 10, Oct. 1985, pp. 1123–1128.

Fink–Bennett, "The Role of Cholecystogogues in the Evaluation of Biliary Tract Disorders," Nuclear Medicine Annual 1985, Lenny Freeman and Heidi Weissman, eds., New York, Raven Press, 1985, pp. 107–132.

Newman et al., "A Simple Technique for Quantitative Cholecystokinin—HIDA Scanning," The British Journal of Radiology, vol. 56, Jul. 1983, pp. 500–502.

Pickleman et al., "The Role of Sincalide Cholescintigraphy in the Evaluation of Patients with Acalculus Gallbaldder Disease," Archives of Surgery, vol. 120, Jun. 1985, pp. 693–697.

Zeissman et al., "Calculation of a Gallbaldder Ejection Fraction: Advantage of Continuous Sincalide Infusion Over the Three–Minute Infusion Method," Journal of Nuclear Medicine, vol. 33, No. 4, Apr. 1992, pp. 537–541.

Balon et al., Society of Nuclear Medicine Procedure Guideline for Hepatobiliary Scintigraphy.

* cited by examiner

Typical Full-Scale and Expanded-Scale Chromatograms of
Reconstituted Kinevac

SINCALIDE FORMULATIONS

FIELD OF THE INVENTION

The invention relates to pharmaceutically acceptable formulations of sincalide.

BACKGROUND OF THE INVENTION

KINEVAC® (Sincalide for Injection, USP) is a cholecystopancreatic-gastrointestinal hormone peptide for parenteral administration. The active pharmaceutical ingredient, 1-De(5-oxo-L-glutamine-5-L-proline)-2-de-L-methioninecaerulein or "sincalide" (CAS# 25126-32-3), is a synthetically prepared C-terminal octapeptide of cholecystokinin (CCK-8), with the following amino acid sequence: Asp-Tyr($SO_3$H)-Met-Gly-Trp-Met-Asp-Phe-$NH_2$.

KINEVAC® was first introduced in 1976, and was finished as a sterile, nonpyrogenic, lyophilized white powder in a 5-mL (nominal) glass vial to contain: 5 μg sincalide with 45 mg sodium chloride to provide tonicity; sodium hydroxide or hydrochloric acid may have been added for pH adjustment (pH 5.5–6.5). The type I glass vial was sealed under a nitrogen headspace with a Tompkins B0849 closure. This two-ingredient formulation was incorporated into the U.S. Pharmacopea/National Formulary, USP 24, NF 19, Jan. 1, 2000.

Since its introduction, various drawbacks in the manufacturing and analysis of KINEVAC® have been identified. For example, the two-ingredient formulation suffers from potency variability. This variability was exacerbated by the fact that the formulation was analyzed using a guinea pig gallbladder contraction bioassay for potency of both sincalide and KINEVAC®. This bioassay was unable to distinguish between bioactivity of sincalide and bioactivity of sincalide degradants. Accordingly, a 20% overage of sincalide was required in previous sincalide formulations to compensate for the limitations of the bioassay. Thus, there is a need for sincalide formulations having improved and consistent potency as established by a sincalide specific assay such as HPLC.

SUMMARY OF THE INVENTION

The present invention satisfies the need for improved sincalide formulations by providing formulations that eliminate the need for a 20% overage of sincalide. The sincalide formulations of the invention are also purer than prior art formulations, and have fewer degradants and more consistent potency. In addition, the purity of these formulations, may be assessed by HPLC, thus eliminating the need for the bioassay of the prior art formulations.

The present invention provides sincalide formulations adapted for administration by injection. These sincalide formulations are characterized by improved stability and may be prepared as a relatively large volume batch (≈100 L).

In one aspect, the invention features sincalide formulations that include an effective amount of sincalide, a bulking agent/tonicity adjuster, one or more stabilizers, a surfactant, a chelator, and a buffer. The invention also features kits and methods for preparing improved sincalide formulations, as well as methods for treating, preventing, and diagnosing gall bladder-related disorders using sincalide formulations.

The formulations of the invention preferably have a pH between 6.0 and 8.0. Suitable buffers include, but are not limited to, phosphate, citrate, sulfosalicylate, borate, acetate and amino acid buffers. Phosphate buffers, such as dibasic potassium phosphate, are preferred.

In various embodiments of the invention, the surfactant is a nonionic surfactant, preferably a polysorbate, such as polysorbate 20 or polysorbate 80; the chelator is pentetic acid (DTPA); and the stabilizer is an antioxidant and/or amino acid. In a particularly desirable embodiment of the invention, the formulation includes a plurality of stabilizers, preferably L-arginine monohydrochloride, L-methionine, L-lysine monohydrochloride, and sodium metabisulfite.

Suitable bulking agents/tonicity adjusters include, but are not limited to, mannitol, lactose, sodium chloride, maltose, sucrose, PEG's, cyclodextrins, dextran, polysucrose (Ficoll), and polyvinylpyrrolidine (PVP). D-Mannitol is a preferred bulking agent/tonicity adjuster.

In a particularly preferred embodiment, the reconstituted formulation includes 0.0008 to 0.0012 mg/mL active ingredient (i.e., sincalide); 20.0 to 50.0 mg/mL mannitol, 2.0 to 7.0 mg/mL arginine; 0.2 to 1.0 mg/mL methionine; 2.0 to 30.0 mg/mL lysine; 0.002 to 0.012 mg/mL sodium metabisulfite; 0.000001 to 0.003 mg/mL polysorbate 20, 0.1 to 3.0 mg/mL pentetic acid (DTPA); and 5.4 to 12.0 mg/mL potassium phosphate (dibasic). In, a more preferred embodiment, the reconstituted formulation includes about 0.001 mg/mL sincalide; about 34 mg/mL D-mannitol, about 6 mg/mL L-arginine monohydrochloride; about 0.8 mg/mL L-methionine; about 3 mg/mL L-lysine monohydrochloride; about 0.008 mg/mL sodium metabisulfite; less than about 0.01 mg/mL polysorbate 20, about 0.4 mg/mL pentetic acid (DTPA); and about 1.8 mg/mL potassium phosphate (dibasic).

The kits of the invention may, for example, include the various components of the formulation as a mixture in powder form, along with a container (e.g., a vial) to hold the powder mixture and a physiologically acceptable fluid for reconstitution of the formulation, The components of the formulation may be present in the kit either in the powder mixture or in the fluid portion. Kits of the invention may also include all components in a liquid mixture or some components in a liquid form and some in the form of a powder.

The formulations of the invention have improved stability and potency compared to previous sincalide formulations, and are useful as diagnostic aids for imaging the hepatobiliary system of a patient. When used as a diagnostic aid, the sincalide formulations may, for example, be co-administered with a radiopharmaceutical agent having rapid hepatic uptake, such as $^{99m}$Tc-mebrofenin, or similar hepatobiliary imaging agents, to assist in the diagnosis of gallbladder diseases and related disorders. Additionally, the formulations may be administered before and/or after diagnostic imaging (including for example, magnetic resonance imaging, scintigraphic imaging, ultrasound imaging, etc.)

The sincalide formulations of the invention may also be administered to patients receiving total parenteral nutrition (TPN), in order to treat and/or prevent TPN-related disorders.

Other features and advantages of the invention will be apparent from the following detailed description thereof and from the claims.

DETAILED DESCRIPTION OF THE INVENTION

Figure 1:
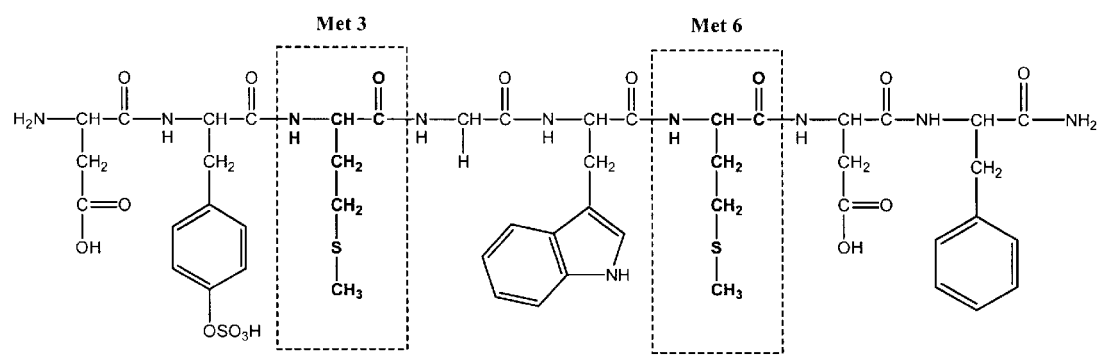
FIG. 1 is a drawing illustrating the chemical structure of 1-De(5-oxo-L-glutamine-5-L-methioninecaerulein or "sincalide" (CAS# 25126-32-3). The amino acid residues "Met 3" and "Met 6" are outlined by dashed lines.

In order to develop an improved sincalide formulation a series of studies, described in the Examples below, were conducted to determine the effects of various excipients on formulations of sincalide. Through these studies, we discovered that the potency and stability of sincalide formulations can be significantly enhanced through the careful selection of excipients that provide certain desired functions. Accordingly, the present invention provides novel sincalide formulations having improved stability and/or potency over previous formulations.

As used herein, the term "sincalide" includes the synthetically-prepared C-terminal octapeptide of cholecystokinin (CCK-8), with the amino acid sequence: Asp-Tyr ($SO_3H$)-Met-Gly-Trp-Met-Asp-Phe-$NH_2$, as well as derivatives thereof which have been optimized or modified (to improve stability, potency, pharmacokinetics, etc.), but retain the biological activity of the original octapeptide. For example, peptides in which the methionine and/or aspartic acid residues have been replaced without significantly affecting the biological activity are included within "sincalide" as the term is used herein. Similarly, the term "sincalide" encompasses not only monomeric, but multimeric forms of the peptide, as well as physiologically active degradants or portions of the peptide and its derivatives.

The sincalide formulations of the invention can include a variety of excipients, such as, for: example, antioxidants, buffers, bulking agents/tonicity adjusters, chelating agents, complexing agents, crosslinking agents, co-solvents, osmolality adjustors, solubilizers, surfactants, stabilizers, pH adjustors, lyoprotectants/cryoprotectants, air/liquid and/or ice-liquid interface protectants (protectants against surface induced denaturation), freeze-thaw protectants, protectants against protein/peptide denaturation, protectants for rehydration, and wetting agents. In preferred embodiments, the formulations include excipients that perform the functions of at least: (i) a bulking agent/tonicity adjuster, (ii) a stabilizer, (iii) a surfactant, (iv) a chelator, and (v) a buffer. Typically, each of these functions is performed by a different excipient. However, in some embodiments of the invention a single excipient may perform more than one function. For example, a single excipient may be multi-functional, e.g. amino acids may function as bulking agents, stabilizers and/or buffers and other excipients may function, for example, as both a stabilizer and a chelator or as both a bulking agent and a tonicity adjuster. Alternatively, multiple excipients serving the same function may be used. For example, the formulation may contain more than one excipient that functions as a stabilizer.

Table 1 below shows the concentration ranges for various excipients that were investigated. In general, the range studies were based on a 2-mL fill of bulk solution per vial before lyophilization. After reconstitution with 5 mL of water for injection the final sincalide formulation results in an isotonic solution. The concentration ranges of the various ingredients provided in Table 1 can be adjusted upward or downward, if necessary in conjunction with: increasing or decreasing the fill volume per vial, obtaining the desired pH, obtaining the desired reconstitution volume, and the desirability of achieving tonicity in the final reconstituted solution. For example, as indicated above, the concentrations provided in Table 1 were developed to provide an isotonic solution; however, one skilled in the art would recognize that a broader range of concentrations could be used if an isotonic solution was not required.

TABLE 1

Concentration ranges for excipients for preferred sincalide formulations.

| Excipient | Function | Range (mg/mL Bulk) | Range (mg/vial) | Range (mg per 1 mL after reconst) | Final Formulation (mg) 1 mL Bulk | 1 vial Target | 1 mL after reconst. |
|---|---|---|---|---|---|---|---|
| (Sincalide) | Active Ingredient | 0.0025 | 0.0050 | 0.0008–0.0012 | 0.0025 | 0.0050 | 0.0010 |
| Mannitol | Bulking Agent/Cake Forming Agent/Tonicity Adjuster | 50.0–125.0 | 100–250 | 20.0–50.0 | 85 | 170 | 34 |
| TWEEN ®-20 | Non-ionic Surfactant/Solubilizing Agent/Wetting Agent | 0.0000025–0.0075 | 0.0000050–0.0150 | 0.0000010–0.0030 | <0.01 | <0.01 | <0.01 |

TABLE 1-continued

Concentration ranges for excipients for preferred sincalide formulations.

| Excipient | Function | Range (mg/mL Bulk) | Range (mg/vial) | Range (mg per 1 mL after reconst) | Final Formulation (mg) 1 mL Bulk | Final Formulation (mg) 1 vial Target | Final Formulation (mg) 1 mL after reconst. |
|---|---|---|---|---|---|---|---|
| DTPA | Chelator/Stabilizer/Antioxidant/Complexing Agent/Preservative/pH Adjuster | 1.0 | 2.0 | 0.1–3.0 | 1.0 | 2.0 | 0.4 |
| Sodium Metabisulfite | Antioxidant/Preservative/Stabilizer | 0.005–0.030 | 0.010–0.060 | 0.002–0.012 | 0.020 | 0.040 | 0.008 |
| Potassium Phosphate, dibasic | Buffer/pH Adjuster/Dissolution Aid | 2.7–4.5 | 5.4–12.0 | 1.1–1.8 | 4.5 | 9.0 | 1.8 |
| Potassium Phosphate, monobasic | Buffer/pH Adjuster/Dissolution Aid | 1.0–6.5 | 9.6–13.0 | 1.92–2.6 | 0 | 0 | 0 |
| Methionine | Stabilizer | 0.5–2.5 | 1.0–5.0 | 0.2–1.0 | 2.0 | 4.0 | 0.8 |
| Lysine | Stabilizer/Lyoprotectant/Cryoprotectant | 5.0–30.0 | 10.0–60.0 | 2.0–30.0 | 7.5 | 15.0 | 3.0 |
| Arginine | Stabilizer/Lyoprotectant/Cryoprotectant/pH Adjuster | 5.0–17.5 | 10.0–35.0 | 2.0–7.0 | 15 | 30.0 | 6.0 |
| Sodium Chloride | Tonicity Adjuster | 4.5–9.0 | 9.0–18.0 | 1.8–3.6 | 0 | 0 | 0 |

Alternative excipients include TWEEN ®-80, potassium metabisulfite, sodium phosphate dibasic, sodium phosphate monobasic, and potassium chloride. Additional alternatives are listed below.

Table 2 shows preferred ranges for preferred excipients in the bulk solutions, vials and after reconstitution. All concentrations shown for the bulk solution are based on a 2 mL fill volume. The ingredient quantities are matched to result in a pH slightly below neutral and result in an isotonic solution after reconstitution of the lyophilized vial as indicated by an osmolality in the range of 180 to 320 mOsm/kg, preferably, 240 to 320 mOsm. The columns titled "Final Formulation" represent particularly preferred formulations.

TABLE 2

Osmolality values for various sincalide formulations.
(All formulations contain 0.0025 mg CCK-8/mL.; "dibasic" and "monobasic" refer to dibasic and monobasic potassium phosphate; "Na meta" refers to sodium metabisulfite)

| Formulation Excipients (mg/mL Bulk) | Calculated mOsm/kg |
|---|---|
| Mannitol (125.0) Dibasic (3.75) DTPA (1.0) | 292 |
| Mannitol (95.0) Dibasic (4.0) Monobasic (2.8) DTPA (1.0) | 244 |
| Mannitol (103.0) Dibasic (3.75) DTPA (1.0) | 244 |
| Mannitol (75.0) NaCl (4.5) Dibasic (3.75) DTPA (1.0) | 244 |
| Mannitol (85.0) TWEEN ® 20 (0.005) Dibasic (2.75) DTPA (1.0) Methionine (2.0) Lysine (15.0) | 187 |
| Mannitol (50.0) | 247 |

TABLE 2-continued

Osmolality values for various sincalide formulations.
(All formulations contain 0.0025 mg CCK-8/mL.; "dibasic" and "monobasic" refer to dibasic and monobasic potassium phosphate; "Na meta" refers to sodium metabisulfite)

| Formulation Excipients (mg/mL Bulk) | Calculated mOsm/kg |
|---|---|
| NaCl (9.0) Dibasic (3.00) DTPA (1.0) TWEEN ® 20 (0.0075) | 264 |
| Mannitol (75.0) KCl (6.0) Dibasic (3.25) Monobasic (1.0) DTPA (1.0) Methionine (2.0) TWEEN ® 20 (0.005) | 264 |
| Mannitol (75.0) KCl (6.0) Dibasic (3.25) Monobasic (1.0) DTPA (1.0) Methionine (2.0) TWEEN ® 20 (0.0025) | 264 |
| Mannitol (75.0) KCl (6.0) Dibasic (3.25) Monobasic (1.0) DTPA (1.0) Methionine (2.0) TWEEN ® 20 (2.5 ng) | 264 |
| Mannitol (85.0) Dibasic (4.50) DTPA (1.0) Na metabisulfite (0.020) Methionine (2.0) Lysine (7.50) Arginine (15.0) | 314 |

TABLE 2-continued

Osmolality values for various sincalide formulations.
(All formulations contain 0.0025 mg CCK-8/mL.; "dibasic" and "monobasic" refer to dibasic and monobasic potassium phosphate; "Na meta" refers to sodium metabisulfite)

| Formulation Excipients (mg/mL Bulk) | Calculated mOsm/kg |
|---|---|
| Na Meta (0.015) Mannitol (85.0) Dibasic (2.75) DTPA (1.0) 20 (0.005) Methionine (2.0) Lysine (7.50) Arginine (15.0) | 257 |
| Na Meta (0.030) Mannitol (85.0) Dibasic (2.75) DTPA (1.0) TWEEN ® 20 (0.005) Methionine (2.0) Lysine (7.50) Arginine (15.0) | 257 |
| Na Meta (0.005) Mannitol (85.0) Dibasic (2.75) DTPA (1.0) TWEEN ® 20 (0.005) Methionine (2.0) Lysine (7.50) Arginine (15.0) | 257 |
| Na Meta (0.020) Mannitol (85.0) Dibasic (3.00) DTPA (1.0) TWEEN ® 20 (0.005) Methionine (2.0) Lysine (7.50) Arginine (15.0) | 259 |
| Dibasic (2.75) Mannitol (85.0) Na Meta (0.015) DTPA (1.0) TWEEN ® 20 (0.005) Methionine (2.0) Lysine (7.50) Arginine (15.0) | 257 |
| Dibasic (3.00) Mannitol (85.0) Na Meta (0.020) DTPA (1.0) TWEEN ® 20 (0.005) Methionine (2.0) Lysine (7.50) Arginine (15.0) | 259 |
| Dibasic (3.25) Mannitol (75.0) KCl (6.0) TWEEN ® 20 (0.0025) Monobasic (1.0) DTPA (1.0) Methionine (2.0) | 264 |
| Dibasic (4.50) Mannitol (85.0) TWEEN ® 20 (2.5 ng) DTPA (1.0) Na metabisulfite (0.020) Methionine (2.0) Lysine (7.50) Arginine (15.0) | 314 |
| Methionine (2.0) Mannitol (75.0) NaCl (5.0) TWEEN ® 80 (0.025) Monobasic (1.0) DTPA (1.0) Dibasic (3.25) | 262 |
| Methionine (1.5) Mannitol (75.0) NaCl (5.0) TWEEN ® 80 (0.025) Monobasic (1.0) DTPA (1.0) Dibasic (3.25) | 262 |
| Methionine (1.0) Mannitol (75.0) NaCl (5.0) TWEEN ® 80 (0.025) Monobasic (1.0) DTPA (1.0) Dibasic (3.25) | 262 |
| Methionine (0.5) Mannitol (75.0) NaCl (5.0) TWEEN ® 80 (0.025) Monobasic (1.0) DTPA (1.0) Dibasic (3.25) | 262 |
| Methionine (2.5) Mannitol (75.0) NaCl (5.0) TWEEN ® 80 (0.005) Monobasic (1.0) DTPA (1.0) Dibasic (3.25) | 262 |
| Lysine (5.0) Mannitol (95.0) TWEEN ® 20 (0.005) Dibasic (2.75) DTPA (1.0) Methionine (2.0) | 209 |
| Lysine (15.0) Mannitol (85.0) TWEEN ® 20 (0.005) Dibasic (2.75) DTPA (1.0) Methionine (2.0) | 187 |
| Lysine (30.0) Mannitol (70.0) TWEEN ® 20 (0.005) Dibasic (2.75) DTPA (1.0) Methionine (2.0) | 245 |
| Arginine (17.5) Mannitol (85.0) TWEEN ® 20 (0.005) Dibasic (2.75) DTPA (1.0) Methionine (2.0) | 245 |
| Arginine (10.0) Mannitol (85.0) TWEEN ® 20 (0.005) Dibasic (2.75) DTPA (1.0) Methionine (2.0) | 232 |
| Arginine (5.0) Mannitol (85.0) TWEEN ® 20 (0.005) Dibasic (2.75) DTPA (1.0) Methionine (2.0) Lysine (7.5) Arginine (8.75) | 238 |
| Mannitol (85.0) TWEEN ® 20 (0.005) Dibasic (2.75) DTPA (1.0) | 245 |

TABLE 2-continued

Osmolality values for various sincalide formulations.
(All formulations contain 0.0025 mg CCK-8/mL; "dibasic"
and "monobasic" refer to dibasic and monobasic potassium
phosphate; "Na meta" refers to sodium metabisulfite)

| Formulation Excipients (mg/mL Bulk) | Calculated mOsm/kg |
|---|---|
| Methionine (2.0) Lysine (7.5) Arginine (15.0) Mannitol (85.0) TWEEN ® 20 (0.005) Dibasic (2.75) DTPA (1.0) Methionine (2.0) Lysine (7.5) | 257 |

Chelators

Excipient impurities and/or stopper extractables can introduce trace metals into pharmaceutical formulations. Sincalide contains two methionine residues (Met 3 and Met 6) that are susceptible to oxidation by free metals. Thus, the sincalide formulations of the invention contain chelators to inhibit the oxidation of the two methionine residues present in sincalide (Met 3 and Met 6). Preferred chelators include pentetic acid (DTPA), edetic acid (EDTA) and derivatives thereof, including salts. DTPA is a preferred chelator. As described in Example 2 below, the amounts of the degradants, sincalide Met 3 and sincalide Met 6 monosulfoxides, increase in the presence of certain metals and in the absence of DTPA, while the presence of DPTA has an inhibitory effect on the formation of these monosulfoxides. In particular, copper and manganese, in the absence of DTPA, have the greatest oxidative effect on the methionine residues of sincalide resulting in combined height percentages of Met 3 and Met 6 monosulfoxides (vs sincalide) of 85.5 and 128.9, respectively.

In a preferred embodiment, the sincalide formulations contain between 0.1 and 3.0 mg of DTPA per mL after reconstitution. In a particularly preferred embodiment, sincalide formulations of the invention contain 0.4 mg DTPA/mL after reconstitution 0 with 5 mL.

Buffering Agents

Buffering agents are employed to stabilize the pH of sincalide formulations of the invention, and consequently, reduce the risk of chemical stability at extreme pH values. Buffering agents useful in the preparation of formulation kits of the invention include, but are not limited to, phosphoric acid, phosphate (e.g. monobasic or dibasic sodium phosphate, monobasic or dibasic potassium phosphate, etc.), citric acid, citrate (e.g. sodium citrate, etc.), sulfosalicylate, acetic acid, acetate (e.g. potassium acetate, sodium acetate, etc.), methyl boronic acid, boronate, disodium succinate hexahydrate, amino acids, including amino acid salts (such as histidine, glycine, lysine, imidazole), lactic acid, lactate (e.g. sodium lactate, etc.), maleic acid, maleate, potassium chloride, benzoic acid, sodium benzoate, carbonic acid, carbonate (e.g. sodium carbonate, etc.), bicarbonate (e.g. sodium bicarbonate, etc.), boric acid, sodium borate, sodium chloride, succinic acid, succinate (e.g. sodium succinate), tartaric acid, tartrate (e.g. sodium tartrate, etc.), tris-(hydroxymethyl)aminomethane, biological buffers (such as N-2-hydroxyethylpiperazine,N'-2-ethanesulfonic acid (HEPES), CHAPS and other "Good's" buffers), and the like.

Phosphate is a preferred buffering agent due to its lack of interaction with sincalide and an ideal buffering capacity in the physiological pH range. Dibasic potassium phosphate is a particularly preferred buffer in sincalide formulations of the invention. As described in Example 1 below, a sincalide formulation of the invention proved to be stable over a pH range of 5.5–9.1. Within the pH range of 5.5–8.5, no distinct pH-dependent related trends in initial sincalide recovery were observed with a sincalide formulation of the invention. Preferably, a sincalide formulation of the invention has a pH from 6.0 to 8.0.

Stabilizers

The octapeptide, sincalide, contains one tryptophan and two methionine residues. Methionine has been identified as one of the most easily oxidizable amino acids, which degrades to its corresponding sulfoxide and, under more strenuous oxidation conditions, its sulfone. The mechanisms of oxidation appear to be highly dependent on the reactive oxygen species under consideration: peroxide, peroxyl radicals, singlet oxygen, and hydroxyl radical have all been shown to oxidize methionine residues to sulfoxides and other products. Therefore, based on the potential for oxidation of this peptide, it was necessary to identify functional additives for peptide stabilization.

Antioxidants/Reducing Agents. In a preferred embodiment of the invention, the sincalide formulation contains an antioxidant or reducing agent as a stabilizer. A wide variety of antioxidants or reducing agents can be used as stabilizers, including but not limited to, acetylcysteine, cysteine, ascorbic acid, benzyl alcohol, citric acid, pentetic acid or diethylenetriamine pentaacetic acid (DTPA), propyl gallate, methylparaben, sulfoxylate, propylparaben, edetic acid or ethylenediaminetetraacetic acid (EDTA), disodium EDTA dihydrate, dithiothreitol, glutathione, monothioglycerol, potassium metabisulfite, sodium formaldehyde sulfoxylate, sodium sulfite, sodium succinate, sodium metabisulfite, stannous chloride, thioacetic acid, thiodiglycerol, thioethanolamine, thioglycolic acid, 2-aminoethanethiol (cysteamine), butylated hydroxyanisole (BHT), and sodium sulfate and derivatives thereof, including salts and sulfurous acid salts. Sodium metabisulfite is a preferred antioxidant stabilizer. Additionally, DTPA, which is a preferred chelator, also may be an antioxidant stabilizer.

Amino Acids. Amino acids have also been used as stabilizers or co-stabilizers of peptides to: act as cryoprotectants during freeze drying, stabilize against heat denaturation, inhibit aggregate formation, improve solubility or rehydration, inhibit isomerization, reduce surface adsorption, or act as chelating agents. They can also increase the product glass transition temperature ($T_g$) and thereby increase process stability, as well as stabilize the product by minimizing overdrying during secondary drying. Surface exposed residues can react readily with oxidizing agents at physiological pH, scavenging oxidizing molecules and protecting critical regions of peptides.

Various D- and/or L-amino acids can be used as stabilizers in sincalide formulations. As used herein "amino acid(s)" and the names of specific amino acids (e.g arginine, lysine, methionine, etc.) encompass D- and/or L-amino acids, amino acid salts, derivatives, homologs, dimers, oligomers, or mixtures thereof. Preferred amino acids for use as stabilizers in the present invention include methionine, lysine, and arginine. Examples of other amino acids (and amino acid salts) suitable as stabilizers include, but are not limited to, arginine glutamate, asparagine, gamma aminobutyric acid, glycine (and glycine buffer), glutamic acid, glutamate, sodium glutamate, histidine (and histidine buffer), lysine glutamate, lysine aspartate, arginine aspartate, imidazole, serine, threonine, alanine, polyglutamic acid, polylysine, glycylglycine and the like, including hydroxypropyl and galactose derivatives. In one particularly preferred embodiment, L-arginine monohydrochloride, L-methionine and L-lysine monohydrochloride are used.

Cryoprotectants/Lyoprotectants

Various cryoprotectants/lyoprotectants can be used in the present invention. Suitable cryoprotectants structure water molecules such that the freezing point is reduced and/or the rate of cooling necessary to achieve the vitreous phase is reduced. They also raise the glass transition temperature range of the vitreous state. These include, but are not limited to: dimethylsulfoxide (DMSO), dextran, sucrose, 1,2-propanediol, amino acids/salts such as, glycine, lysine, arginine, aspartic acid, histidine, proline, etc., glycerol, sorbitol, sodium chloride, fructose, trehalose, raffinose, stachychose, propylene glycol, 2,3-butanediol, hydroxyethyl starch, polyvinylpyrrolidone (PVP), PEG's and similar compounds, protein stabilizers, such as human serum albumin, bovine serum albumin, bovine gamma globulin, gelatin (or derivatives, such as Prionex, etc.), dextrose, glucose, maltose, arabinose, lactose, inositol, polyols (such as sorbitol, xylitol, erithritol, glycerol, ethylene glycol, etc.), tetramethylglucose, sodium sulfate, cyclodextrins and combinations thereof. Lysine and arginine are preferred cryoprotectants/lyoprotectants.

Surfactants/Solubilizers/Surface Active Agents

Peptides are susceptible to physical degradation through denaturation, aggregation, precipitation, container surface adsorption and/or agitation induced denaturation. The addition of a nonionic surfactant, such as polysorbate, to the formulation, may reduce the interfacial tension or aid in solubilization thus preventing or reducing denaturation and/or degradation at air/liquid or liquid/solid interfaces of the product in solution.

Surfactants/solubilizers include compounds such as free fatty acids, esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and triglycerides of saturated or unsaturated fatty acids; glycerides or soya-oil and sucrose; sodium caprolate, ammonium sulfate, sodium dodecyl sulfate (SDS), Triton-100 and anionic surfactants containing alkyl, aryl or heterocyclic structures.

Examples of preferred surfactants/solubilizers for use in the present invention include, but are not limited to, pluronics (e.g., Lutrol F68, Lutrol F127), Poloxamers, SDS, Triton-100, polysorbates such as TWEEN® 20 and TWEEN® 80, propylene glycol, PEG and similar compounds, Brij58 (polyoxyethylene 20 cetyl ether), cremophor EL, cetyl trimethylammonium bromide (CTAB), dimethylacetamide (DMA), NP-40 (Nonidet P-40), and N-methyl-2-pyrrolidone (Pharmasolve), glycine and other amino acids/amino acid salts and anionic surfactants containing alkyl, aryl or heterocyclic structures, and cyclodextrins. TWEEN® 20 is the most preferred surfactant in formulations of the invention.

Bulking Agents/Tonicity Adjusters

Due to the small amount of sincalide present in the formulations of the invention, bulking agents/tonicity adjusters are useful to provide structure and support for the active ingredient, sincalide, as well as to provide tonicity. Bulking agents/tonicity adjusters (also called lyophilization aids) useful in the preparation of lyophilized products of the invention are known in the art and include mannitol, lactose, potassium chloride, sodium chloride, maltose, sucrose, PEG's (such as, for example, PEG 300, PEG 400, PEG 3350, PEG 6000, PEG 8000 and the like, etc.), trehalose, raffinose, dextrose, polygalacturonic acid galacturonic acid, amino acids (including amino acid salts) such as lysine, arginine, glycine, galactose, etc.), cyclodextrins, such as hydroxypropyl-γ-cyclodextrin (HP-γ-CD), dextran, Ficoll, and polyvinylpyrrolidone (PVP). Of these, D-mannitol is the most preferred bulking agent/tonicity adjuster for use with the invention.

Other Excipients

Other excipients, which may optionally be used in the formulations of the invention include preservatives (e.g., benzalkonium chloride), osmolality adjusters (e.g., dextrose), lyoprotectants (e.g., sodium sulfate), solubilizers, tonicity adjusters (e.g. sodium chloride), cake forming agents, complexing agents, and dissolution aids. A listing of various excipients that can be used in sincalide formulations for parenteral administration can be found in, for example, *The Handbook of Pharmaceutical Additives*, Second Edition, edited by Michael & Irene Ash; *Remington's Pharmaceutical Sciences*, (18$^{th}$ Edition), edited by A. Gennaro, 1990, Mack Publishing Company, Easton, Pa. and Pollock et al.; Strickly, Robert G., Parenteral Formulations of Small Molecules Therapeutics Marketed in the United States (I 999)-Part I, *PDA Journal of Pharmaceutical Science and Technology*, 53(6):324 (1999); Strickly, Robert G., Parenteral Formulations of Small Molecules Therapeutics Marketed in the United States (1999)-Part II, *PDA Journal of Pharmaceutical Science and Technology*, 54(1):69 (2000); Parenteral Formulations of Small Molecules Therapeutics Marketed in the United States (1999)-Part III, *PDA Journal of Pharmaceutical Science and Technology*, 54(2): 154 (2000); Nema, Sandeep, et al., Excipients and Their Use in Injectable Products, *PDA Journal of Pharmaceutical Science and Technology*, 51(4): 166 (1997); Wang, Y. J., et al., Parenteral Formulations of Proteins and Peptides: Stability and Stabilizers (Technical Report No. 10), *Journal of Parenteral Science and Technology*, Vol.42 (2S), Supplement 1988; Carpenter, J. et al., Freezing- and Drying-Induced Perturbations of Protein Structure and Mechanisms of Protein Protection by Stabilizing Additives, in *Drugs and The Pharmaceutical Sciences*, Louis Rey and Joan C. May., eds., Marcel Dekker, Inc. New York, N.Y. (1999); Michael J. Pikal, Mechanisms of Protein Stabilization During Freeze-Drying and Storage: The Relative Importance of Thermodynamic Stabilization and Glassy State Relaxation Dynamics, in *Drugs and The Pharmaceutical Sciences*, Louis Rey and Joan C. May., eds., Marcel Dekker, Inc. New York, N.Y. (1999); Shah, D., et al., The Effects of Various Excipients on the Unfolding of Basic Fibroblast Growth Factor, *PDA Journal of Pharmaceutical Science & Technology*, 52(5):238 (1998); Powell, M. F., et al., Compendium of Excipients for Parenteral Formulations, *PDA Journal of Pharmaceutical Science & Technology*, 52(5) :238 (1998); and Inactive Ingredient Guide, Div. Of Drug Information Resources, FDA, CDER, Jan. 1996; Handbook of Injectable Drugs, Edition 8, Am. Soc. Hospital Pharmacists, 1994, L. A. Trissel.

Formulation Kits

Kits of the present invention preferably comprise one or more vials containing the sterile formulation of a predetermined amount of sincalide, a lyophilization aid or bulking.

agent/tonicity adjuster, one or more stabilizers, a surfactant, a chelator, and a buffer. The one or more vials that contain all or part of the formulation can independently be in the form of a sterile solution or a lyophilized solid. Buffering agents useful in the preparation of formulation kits of the invention are discussed herein and include, for example phosphate, citrate, sulfosalicylate, and acetate, and amino acids (including amino acid salts). Dibasic potassium phosphate is a preferred buffer in sincalide formulations of the invention. The kits may also include a fluid portion, for example water or saline, for reconstitution of the formulation prior to injection.

Lyophilization aids or bulking agent/tonicity adjusters useful in the preparation of lyophilized kits include those dicussed above, particularly, mannitol, lactose, sodium chloride, maltose, sucrose, PEG's, galaturonic acid, polygalcturonic acid, cyclodextrins, such as hydroxypropyl-γ-cyclodextrin (HP-γ-CD) and the like, dextran, amino acids (including amino acid salts), Ficoll, and polyvinylpyrrolidone (PVP). Of these, mannitol, sodium chloride, maltose, sucrose, PEG's, HP-γ-CD, and dextran are preferred bulking agents/tonicity adjusters for use with the invention, with mannitol being the most preferred.

As discussed, a component in a formulation kit can also serve more than one function. For example, an excipient which serves as a stabilizer may also serve as the chelator and an excipient which serves as a bulking agent may also serve as a tonicity adjuster. In addition, in some embodiments, the excipients are all in dry powder form, or all in liquid form while in other embodiments, some of the excipients are in dry form and others are in a fluid portion included in or sold separately from the kit.

A particularly preferred kit of the invention contains: about 0.005 mg sincalide, about 170 mg D-mannitol, less than or equal to 0.01 mg TWEEN® 20, about 2 mg DTPA, about 0.04 mg sodium metabisulfite, about 9 mg potassium phosphate (dibasic) about 4 mg L-methionine, about 15 mg L-lysine monohydrochloride, and about 30 mg L-arginine monohydrochloride.

Therapeutic/Diagnostic Uses

Sincalide is a synthetic analog of the endogenously produced hormone cholecystokinin (CCK-8). CCK-8 acts on receptors within the gallbladder wall causing it to contract, cleaning out any remaining sludge or bile that may have accumulated within the gallbladder. CCK-8 increases bile flow and small and large bowel motility, causes the pyloric sphincter to contract and increases pancreatic enzyme secretion. CCK-8 also causes delayed biliary to bowel transit. Sincalide has a more rapid physiologic effect on the gallbladder in terms of contraction and relaxation than the endogenous hormone (CCK-8) produced by the body, making sincalide formulations useful as diagnostic aids for hepatobiliary imaging, when administered alone or in conjunction with a hepatobiliary imaging agent. For example, sincalide may be administered before and/or after diagnostic imaging (such as, for example, magnetic resonance imaging, scintigraphic imaging, ultrasound imaging, etc.) to improve visualization and/or diagnosis of various disease states.

In one embodiment, hepatobiliary imaging can be performed using, for example, hepatobiliary scintigraphy, an instrumental imaging tool used in the diagnosis and evaluation of hepatobiliary disease. Detection of diseases, such as acute and chronic cholecystitis, biliary obstruction, bile leaks, and other forms of hepatobiliary disease, help the physician to better determine the appropriate course of treatment and management of the patient suffering from a suspected hepatobiliary pathology.

As explained below, the indications for use of sincalide in conjunction with hepatobiliary imaging include (a) pretreatment of patients who have not eaten for more than 20 to 24 hours prior to imaging (in order to empty the gallbadder (GB) of non-radiolabelled bile) and (b) use in the analysis of gallbladder motor function, including the determination of GBEF (gallbladder ejection fraction).

It is important to properly prepare the patient prior to hepatobiliary imaging in order to achieve high quality imaging and reduce the number of false positive and negative results. Preferably, patients should have nothing to eat for 4 to 12 hours prior to hepatobiliary imaging. Prolonged fasting, however, may result in false positive test results (i.e. failure to visualize the gallbladder). If a patient has not eaten for more than 24 hours, the patient is preferably pretreated with sincalide by administration of the sincalide formulation described herein prior to imaging. Typically, the gallbladder contracts within 15 minutes after sincalide injection and the hepatobiliary imaging agent (e.g., radiotracer) is injected 30 minutes later. The gallbladder is then emptied and is better able to take up and accumulate imaging agent (e.g., radiotracer), which helps to reduce the number of false positive studies.

The preferred radiopharmaceuticals used for hepatobiliary imaging include, but are not limited to, Tc 99m IDA (Iminodiacetic acid) analogs, such as Tc-99m mebrofenin (CHOLETEC®), Tc-99m disofenin (DISIDA), and Tc-99m lidofenin (see also U.S. Pat. No. 4,418,208). Tc-99m mebrofenin is a preferred hepatobiliary imaging agent. Methods for coadministration of Tc 99m IDA (Iminodiacetic acid) analogs with CCK and sincalide are known in the art and described in, for example, Ziessman H A., Cholecystokinin cholescintigraphy: victim of its own success? J. Nucl. Med. 1999, 40:2038–2042; Krishnamurthy S., et al., Gallbladder ejection fraction: A decade of progress and future promise. J. Nucl. Med. 1992, 32:542–544; Krishnamurthy G T., et al., Quantitative biliary dynamics: introduction of a new noninvasive scintigraphic technique. J. Nucl. Med. 1983;24:217–223; Mesgarzadeh M., et al., Filling, post-cholecystokinin emptying and refilling of normal gallbladder: effects of two different doses of CCK on refilling: Concise Comm. J. Nucl. Med. 1983, 24:666–671; Krishnamurthy G T., et al., The gallbladder emptying response to sequential exogenous cholecystokinin, Nucl. Med. Corn., 1984, 5 (1) pp 27–33; Krishnamurthy G T., et al., Detection, localization, and quantitation of degree of common bile duct obstruction by scintigraphy, J. Nucl. Med. 1985, 26:726–735; Fink-Bennet D., et al., Cholecystokinin cholescintigraphic findings in the cystic duct syndrome, J. Nucl. Med. 1985, 26:1123–1128; Fink-Bennet D., The role of cholecystogogues in the evaluation of biliary tract disorders. Nucl. Med. Ann. 1985, Lenny Freeman and Heidi Weissman, eds., New York, Raven Press, 1985, pp. 107–132; Newman P., et al., A simple technique for quantitation cholecystokinin-HIDA scanning. British J. of Radiology, vol. 56, pp. 500–502, 1983; Pickleman J., et al. The role of sincalide cholescintigraphy in the evaluation of patients with acalculous gallbladder disease. Archives of Surgery, vol. 120, 693–697; Ziessman, H A., et al., Calculation of a gallbladder ejection fraction: Advantage of continuous sincalide infusion over the three-minute infusion method. J. Nucl. Med. 1992, 33:537–41; Sitzmann, J V., et al., Cholecystokinin prevents parenteral nutrition induced biliary sludge in humans, Surg. Gynecol. Obstet. 170:25–31, 1990; Teitelbaum D H., et al., Treatment of parenteral nutrition-associated cholestasis with cholecystokinin-octapeptide. J. Pediatr. Surg. 30:1082, 1995.

After administration of the hepatobiliary imaging agent, the hepatobiliary system of the patient can be imaged using an appropriate detection device. When a Tc-99m IDA (Iminodiacetic acid) analog, such as CHOLETEC® is used as an imaging agent, a gamma camera can be employed to scan the body of the patient for radioactivity. Imaging of the gallbladder allows for the non-invasive measurement and analysis of various biliary motor functions, including the gallbladder ejection fraction (GBEF). Measurement of GBEF is clinically valuable in the diagnosis and management of certain gallbladder-related disorders, including chronic acalclulous cholecystitis (CAC). In particular, low GBEF has been found to have a >90% positive predictive value for CAC. Other changes in biliary dynamics may be used in the diagnosis of a variety of biliary disorders.

Methods for determining GBEF scintigraphically are known in the art, and are o described in, for example, the references cited above. Sincalide aids in the analysis of biliary function, including the measurement of GBEF, through its physiological effects on the gallbladder, e.g. it ability to induce gallbladder contraction and emptying. One technique for measuring GBEF is to administer sincalide slowly as a 1–3 minute infusion and to calculate GBEF at the end of about 20 minutes. Alternatively, sincalide may be infused rapidly as a bolus, or as a slower continuous infusion ranging from 15 to 60 minutes. By inducing certain biliary functions during hepatobiliary imaging, sincalide aids in the identification of anomalies in such functions, which may be indicative of certain hepatobiliary diseases.

Administration of sincalide formulations can be via IV or IM injections: For IV administration the dose can be administered as a bolus or slow injection over time optionally with the aid of an infusion pump. The dose for IV administration is typically 0.005 to 0.04 $\mu$g/kg (bolus injection) or 0.005 $\mu$g/kg in a series of 4- three minute injections. A dose of 0.02–0.04 tg/kg IV over 2–3 minutes, but up to 1 hour is described in the art. Injection rates of 0.58 $\mu$g/kg/ hour can also be employed with the use of an infusion pump. Other regimens starting at 10 ng/kg/hr and increasing to 160 ng/kg/hr are also known in the art. Bolus injection is not recommended in every case, but injection of 0.02 to 0.04 $\mu$g/kg over 2–3 minutes even up to 15 min. can be used to avoid spasm of the cystic duct or GB.

Doses for IM administration are generally higher and range from 0.1 to 0.4 $\mu$g/kg. In one embodiment the 0.4 $\mu$g/kg IM dose is generally preferred resulting in the greatest GB response with the fewest side effects. Further details on administration are provided in, for example, Mesgarzadeh M., et al., Filling, post cholecystokinin emptying and refilling of normal gallbladder: effects of two different doses of CCK on refilling, J. Nucl. Med. 1983, 24:666–671; Ziessmann H A., et al., Calculation of a gallbladder ejection fraction: Advantage of continuous sincalide infusion over the three-minute infusion method. J. Nucl. 1992, 33:537–541; Pickleman J, et al., The role sincalide cholescintigraphy in the evaluation of patients with acalculous gallbladder disease. Archives of Surgery, vol. 120, 693–697; Krishnamurthy G T., et al., The gallbladder emptying response to sequential exogenous cholecystokinin, Nucl. Med. Corn., 1984, 5 (1) pp 27–33; Krishnamurthy G T., et al., Quantitative biliary dymanics: introduction of a new noninvasive scintigraphic technique. J. Nucl. Med. 1983, 24:217–223; Fink-Bennet D., The role of cholecystogogues in the evaluation of biliary tract disorders. Nucl.Med. Ann. 1985, Lenny Freeman and Heidi Weissman, eds., New York, Raven Press, 1985, pp. 107–132; Balon H. R., et al. Society of Nuclear Medicine procedure guideline for hepatobiliary scintigraphy.

The sincalide formulations of the invention are also useful for treating patients receiving total parenteral nutrition (TPN). TPN induces biliary sludge, the development of cholestasis, and the formation of gall stones and other gallbladder related complications. Indeed, TPN associated cholestatis (TPN-AC) can be a fatal in some instances. The clinical implications of TPN-AC include increased rates of sepsis, cirrhosis, declined lymphocyte function, obstructive jaundice, liver failure, and increased mortality. Although the mechanisms by which these disorders develop have not been definitely established, biliary stasis, the reduction in gallbladder emptying, bile flow, and bile acid secretion that accompanies TPN, has been implicated in the pathogenesis of TPN-AC and other TPN-associated complications. By promoting biliary contraction and emptying, the administration of sincalide to a TPN patient can help to treat and prevent diseases and other complications associated with prolonged TPN.

For TPN patients the dose of 0.05 $\mu$g/kg is typically given IV over 10 minutes as a daily infision. In infants, to treat high bilirubin levels the dose is 0.02 $\mu$g/kg IV or IM twice or 3 times daily with doses increasing up to 0.32 $\mu$g/kg. CCK induces not only GB contraction but also increases intrahepatic bile flow. Information on the treatment of TPN-patients is provided in, for example, Sitzmann, J V., et al., Cholecystokinin prevents parenteral nutrition induced biliary sludge in humans, Surg. Gynecol. Obstet. Vol. 170:25–31, 1990; Moss R L., et al., New approaches to understanding the etiology and treatment of total parenteral nutrition-associated cholestasis, Surg. Gynecol. Obstet. Vol. 8:140–147, 1999; Teitelbaum D H., et al., Treatment of parenteral nutrition-associated cholestasis with cholecystokinin-octapeptide. J. Pediatr. Surg. 30:1082, 1995; Teitelbaum D H. Parenteral nutrition-associated cholestasis, Current Opinion in Pediatrics 1997, 9:270–275; Teitelbaum D H., et al., Parenteral nutrition-associated cholestasis. Seminars in Pediatric Surgery, Vol. 10, pp. 72–80.

The present invention is illustrated by the following examples, which are in no way intended to be limiting of the invention.

EXAMPLE 1

Effect of Buffering Agent and Formulation pH on Sincalide Formulations

Experiments were conducted to determine the effect of pH on the chemical stability of sincalide. Chemical instability, or degradation, may be caused by, for example, oxidation, reduction, deamidation, hydrolysis, imide formation, racemization, isomerization, and/or β-elimination. To examine the effect of pH on sincalide in phosphate buffer solution, solutions of sincalide ($\approx$1.7 $\mu$g/mL) were prepared in 35 mM phosphate buffer and pH-adjusted with either dilute HCl or NaOH for final pH values ranging from 3.0–9.1. Using reverse-phase HPLC (RP-HPLC) with gradient elution and UV detection at 215 nm, sincalide stability in solution was assessed by measuring the recovery of sincalide at 0, 6, and 24 hours after pH adjustment.

Figure 5:
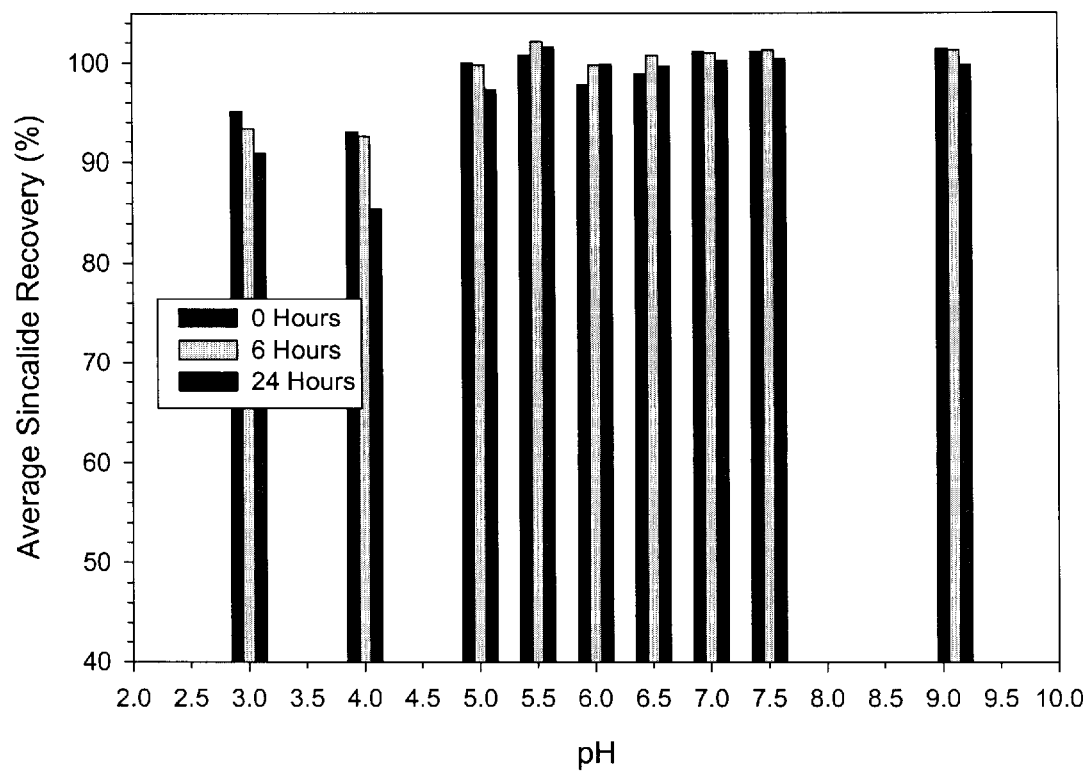
FIG. 5 is a graphical representation of the effect of pH on the recovery of sincalide in 35 mM phosphate buffer over 24 hours. At each pH for which data is shown, the bars represent 0, 6, and 24 hours, from left to right.

Results of the 24-hour study on the stability of sincalide in phosphate buffer over the pH range of 3.0–9.1 are summarized in Table 3 and also represented graphically in FIG. 5. By measure of the percentage recovery, sincalide was stable in 35 mM phosphate buffer solution at pH values ranging from 5.0–9.1 over a 24-hour period. At pH values <5.0, sincalide degradation was evident even at the initial time point.

TABLE 3

Results of pH Study of Sincalide in 35 mM Phosphate Buffer

| | | Average % Sincalide Recovery | | |
|---|---|---|---|---|
| pH | n | 0 Hours | 6 Hours | 24 Hours |
| 3.0 | 2 | 95.2 ± 0.4 | 93.4 ± 0.4 | 90.8 ± 1.2 |
| 4.0 | 2 | 93.0 ± 0.6 | 92.6 ± 1.6 | 85.5 ± 3.0 |
| 5.0 | 4 | 100.0 ± 2.7 | 99.8 ± 1.3 | 97.3 ± 1.8 |
| 5.5 | 2 | 100.7 ± 0.0 | 102.1 ± 0.3 | 101.6 ± 0.6 |
| 6.0 | 2 | 97.8 ± 0.4 | 99.8 ± 0.2 | 99.8 ± 1.0 |
| 6.5 | 2 | 98.8 ± 0.4 | 100.7 ± 0.3 | 99.6 ± 0.1 |
| 7.0 | 2 | 101.0 ± 0.0 | 101.0 ± 1.8 | 100.2 ± 1.2 |
| 7.5 | 2 | 101.0 ± 0.2 | 101.2 ± 0.8 | 100.4 ± 0.0 |
| 9.1 | 5 | 101.3 ± 2.3 | 101.1 ± 1.6 | 99.7 ± 0.9 |

Based on the results shown in Table 3, phosphate was selected as the buffering agent of choice due to a lack of interaction with sincalide and an ideal buffering capacity in the physiological pH range. Subsequently, experiments using phosphate in the formulation shown in Table 4 over the stable pH range established above were performed. Briefly, solutions of sincalide containing the following components (in the concentrations indicated in Table 4) were prepared: sincalide, D-mannitol, L-arginine, L-methionine, L-lysine, sodium metabisulfite, polysorbate 20, pentetic acid and dibasic potassium phosphate.

TABLE 4

Components of a Sincalide Formulation for Example 1

| Component | Concentration (mg/vial) | Function |
|---|---|---|
| Sincalide | 0.0050 | Active |
| D-Mannitol | 170.0 | Bulking Agent/Tonicity Adjuster |
| L-Arginine Monohydrochloride | 30.0 | Stabilizer |
| L-Methionine | 4.0 | Stabilizer |
| L-Lysine Monohydrochloride | 15.0 | Stabilizer |
| Sodium Metabisulfite | 0.040 | Stabilizer |
| Polysorbate 20 (TWEEN ®-20) | <0.01 | Surfactant |
| Pentetic Acid (DTPA) | 2.0 | Chelator |
| Dibasic Potassium Phosphate | 9.0 | Buffer |

Figure 6:
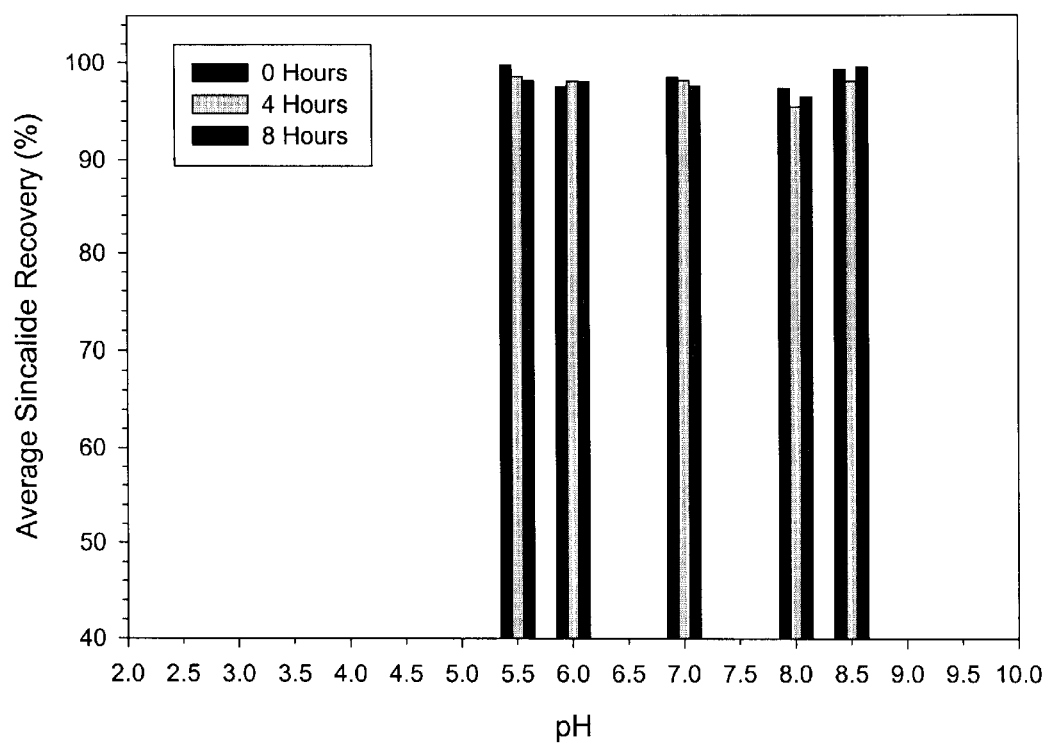
FIG. 6 is a graphical representation of the effect of pH on the recovery of sincalide in a formulation of the invention over 8 hours. At each pH for which data is shown, the bars represent 0, 4, and 8 hours, from left to right.

Solutions were pH-adjusted from 5.5–8.5 with dilute HCl or NaOH, and were evaluated for stability by measuring the sincalide recoveries at 0, 4, and 8 hours after pH adjustment, using RP-HPLC with gradient elution and UV detection at 215 nm, as described above. The results of an 8-hour study on the stability of sincalide in the above formulation over the pH range of 5.5–8.5 are summarized in Table 5 and also represented graphically in FIG. 6.

TABLE 5

Results of pH Study of a Preferred Lyophilized Sincalide Formulation of the Invention

| | | Average % Sincalide Recovery | | |
|---|---|---|---|---|
| pH | n | 0 Hours | 4 Hours | 8 Hours |
| 5.5 | 2 | 99.7 ± 0.2 | 98.5 ± 0.1 | 98.1 ± 0.0 |
| 6.0 | 2 | 97.4 ± 0.5 | 98.0 ± 0.1 | 98.0 ± 0.2 |
| 7.0 | 2 | 98.4 ± 0.1 | 98.1 ± 0.1 | 97.5 ± 1.3 |
| 8.0 | 2 | 97.2 ± 0.6 | 95.4 ± 0.4 | 96.4 ± 0.2 |
| 8.5 | 1, 2, 2 | 99.2 | 98.0 ± 0.0 | 99.5 ± 0.9 |

No distinct pH-dependent related trends in initial sincalide recovery were observed over the pH range studied. Any fluctuation in sincalide recovery over time can be attributed to normal assay variability and not degradation. Sincalide stability in this formulation is further supported by analyses of the chromatographic profiles for the presence of sincalide-related degradants which were consistent at 1.2–1.6% (impurity index) over the 8-hour study from pH 5.5–8.5. A bulk batch solution of sincalide formulation was prepared containing 25 mM phosphate, as a buffering agent, at a target pH value of 6.8 (range 6.7–6.9). Reconstitution of the lyophile with 5 mL of water is equivalent to 10 mM phosphate in the drug product. The data demonstrate solution stability over a physiologically compatible pH range and support a preferred pH of 6.0–8.0 for reconstituted sincalide.

EXAMPLE 2

Effect of Chelators on Sincalide Formulations

Figure 2:
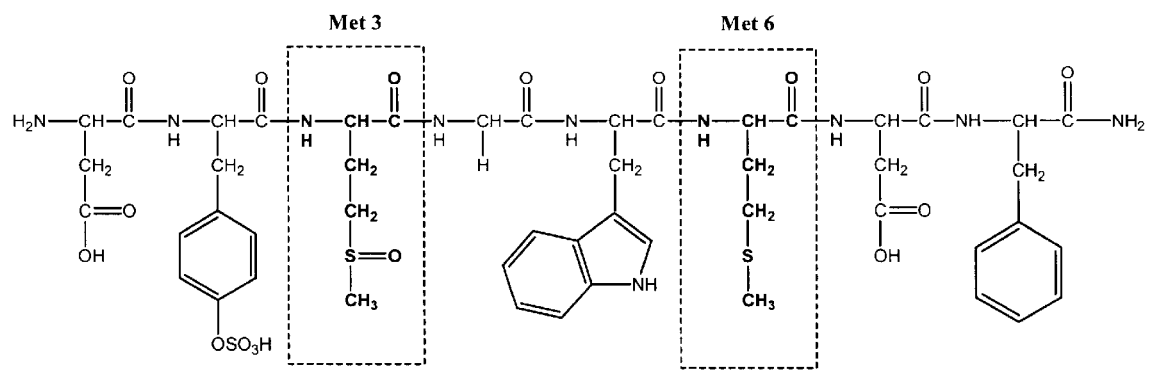
FIG. 2 is a drawing illustrating the chemical structure of sincalide (Met 3) monosulfoxide.
Figure 3:
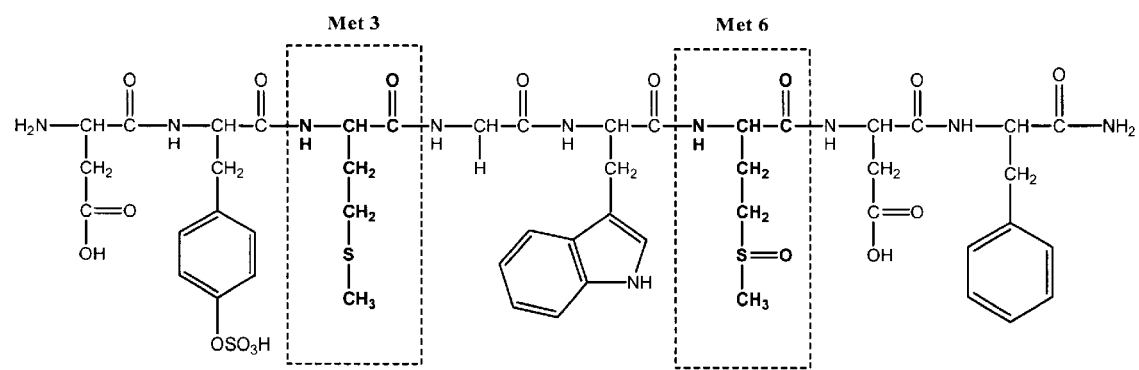
FIG. 3 is a drawing illustrating the chemical structure of sincalide (Met 6) monosulfoxide.
Figure 4:
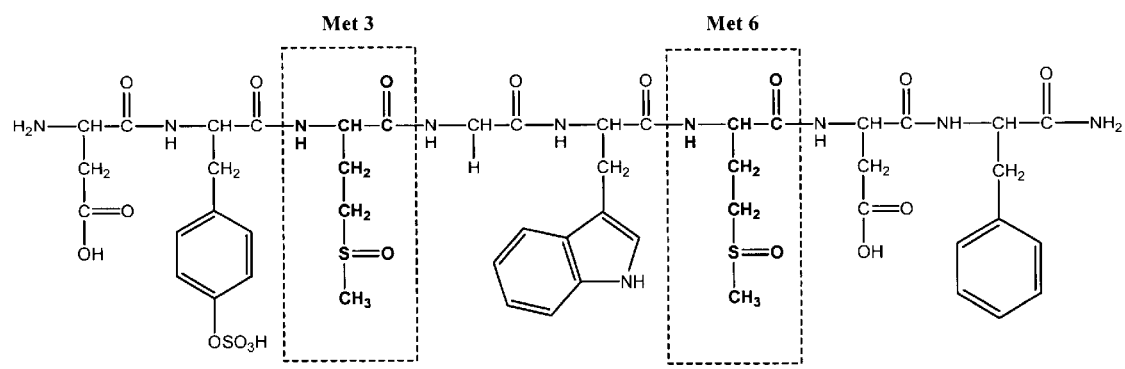
FIG. 4 is a drawing illustrating the chemical structure of sincalide (Met 3, 6) disulfoxide.

As shown in FIG. 1, the amino acid composition of sincalide includes two methionine (Met) residues which are designated as Met 3 and Met 6 in the structural sequence. Experiments were performed to determine whether these residues, as present in sincalide, were susceptible to oxidation by free metals. These experiments also examined the role of DTPA as a formulation excipient to chelate metals and thereby inhibit sincalide oxidation. FIGS. 2–4 show the three oxidized forms of sincalide containing either mono- or disulfoxides. As shown in Table 6, experimental formulations (without amino acids) at pH 6.5–7.0, with 1 mM DTPA (0.39 mg DTPA/mL) and without DTPA were prepared to evaluate potential oxidative effects due to the presence of metals.

TABLE 6

Sincalide Formulations Used in Example 2 (without Amino Acids)

| Component | Concentration (mg/vial) | Bulk Concentration (mg/mL) |
|---|---|---|
| Sincalide | 0.0050 | 0.0025 |
| D-Mannitol | 170.0 | 85.0 |
| L-Arginine Monohydrochloride | 0 | 0 |
| L-Methionine | 0 | 0 |
| L-Lysine Monohydrochloride | 0 | 0 |
| Sodium Metabisulfite | 0.040 | 0.02 |
| Polysorbate 20 | <0.01 | $2.5 \times 10^{-6}$ |
| Pentetic Acid (DTPA) | (+)/(−) | 1.0/0 |
| Dibasic Potassium Phosphate | 9.0 | 4.5 |

The experimental formulation (25 mL) solution with (+) and without (−) DTPA were individually spiked with nine metal ions, as summarized in Table 7.

TABLE 7

Evaluation of Metal Ions for Oxidative Effects on Sincalide

| Metal | Volume (µL) of Metal Ion Standard | Metal Ion Concentration | 1 mM DTPA (+) with/ (−) without |
|---|---|---|---|
| Aluminum ($Al^{3+}$) | 100 | 1.48 mM<br>40 ppm | +<br>− |
| Chromium ($Cr^{3+}$) | 25 | 0.19 mM<br>10 ppm | +<br>− |
| Copper ($Cu^{2+}$) | 100 | 0.63 mM<br>40 ppm | +<br>− |
| Jron ($Fe^{3+}$) | 25 | 0.18 mM<br>10 ppm | +<br>− |

TABLE 7-continued

Evaluation of Metal Ions for Oxidative Effects on Sincalide

| Metal | Volume (μL) of Metal Ion Standard | Metal Ion Concentration | 1 mM DTPA (+) with/ (−) without |
|---|---|---|---|
| Lead ($Pb^{2+}$) | 100 | 0.19 mM<br>40 ppm | +<br>− |
| Magnesium ($Mg^{2+}$) | 50 | 0.82 mM<br>20 ppm | +<br>− |
| Manganese ($Mn^{2+}$) | 25 | 0.18 mM<br>10 ppm | +<br>− |
| Nickel ($Ni^{2+}$) | 100 | 0.68 mM<br>40 ppm | +<br>− |
| Zinc ($Zn^{2+}$) | 100 | 0.61 mM<br>40 ppm | +<br>− |

Figure 7:
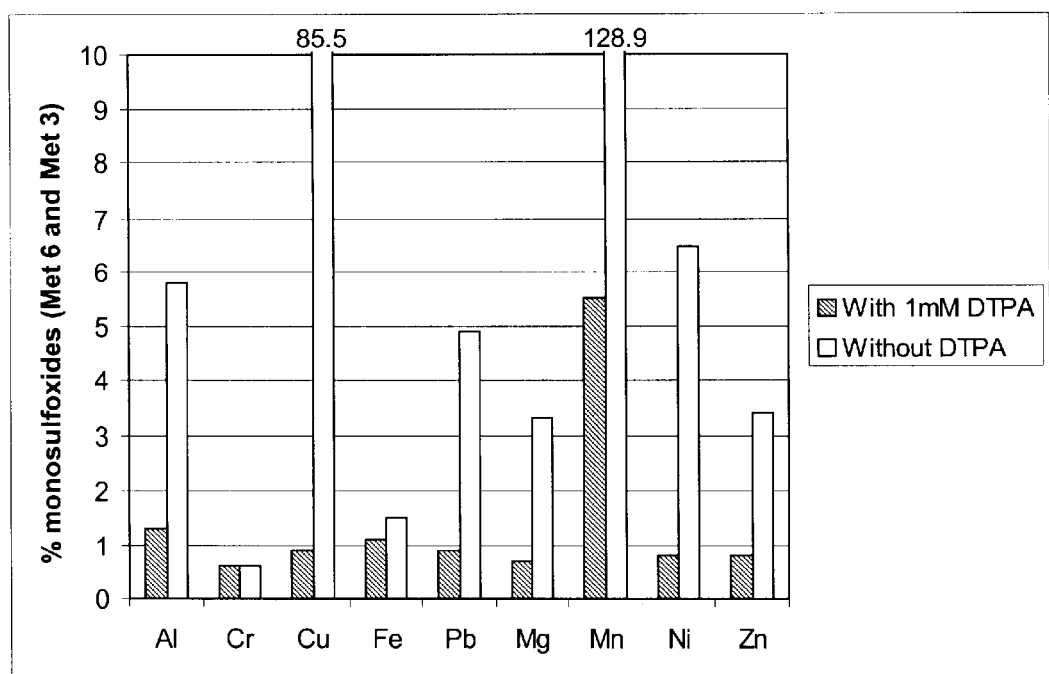
FIG. 7 is a graphical representation of the percent sincalide Met 3 and Met 6 monosulfoxides (vs sincalide), in the presence and absence of pentetic acid (DTPA).
Figure 8:
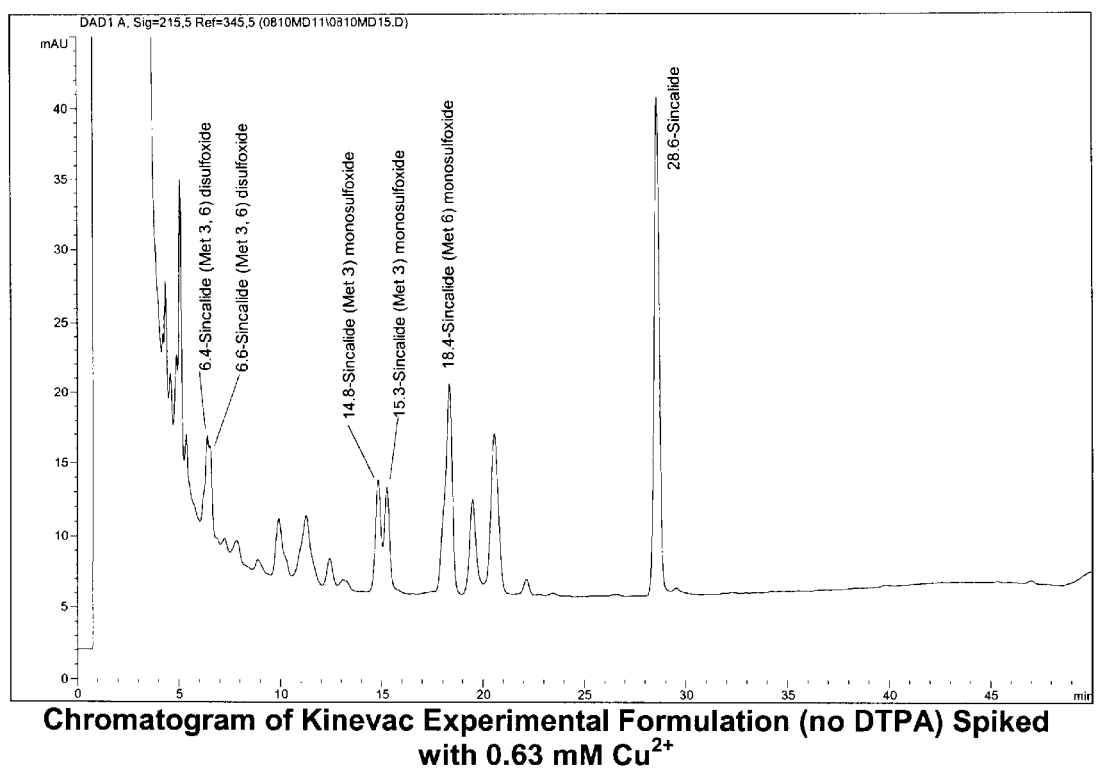
FIG. 8 is a chromatogram of KINEVAC® experimental formulation (no DTPA) spiked with 0.63 mM $Cu^{2+}$.
Figure 9:
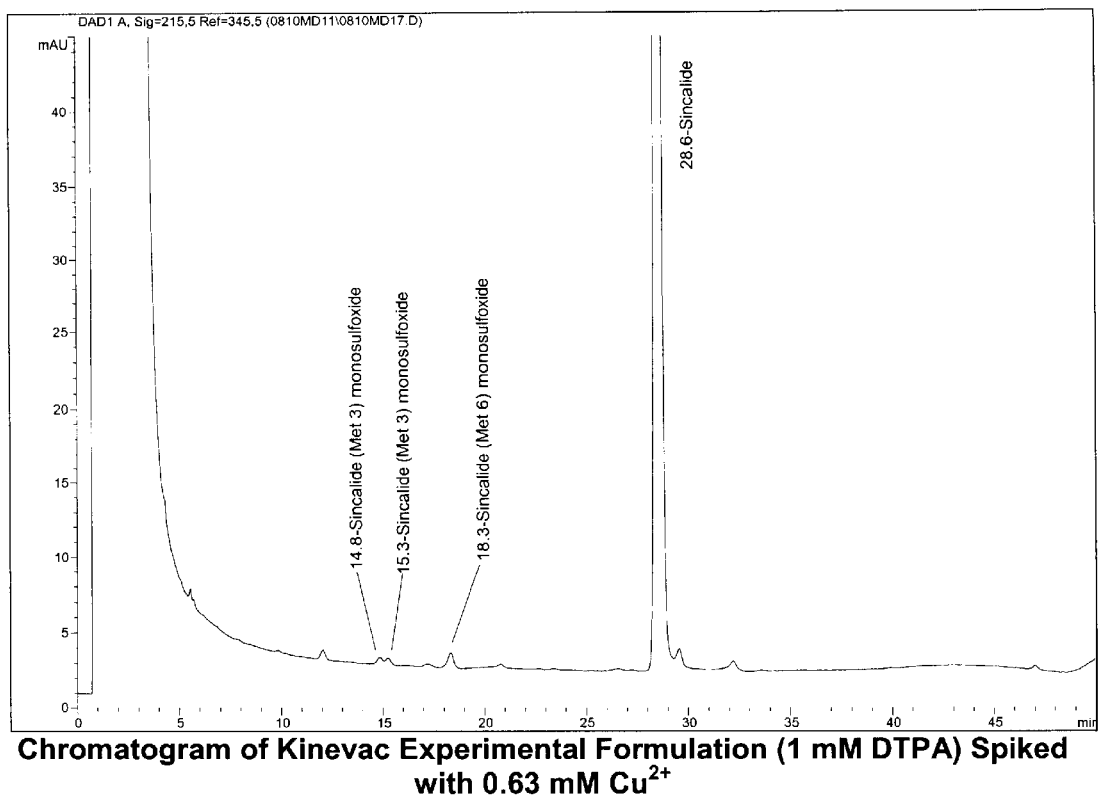
FIG. 9 is a chromatogram of KINEVAC® experimental formulation (1 mM DTPA) spiked with 0.63 mM $Cu^{2+}$.
Figure 10:
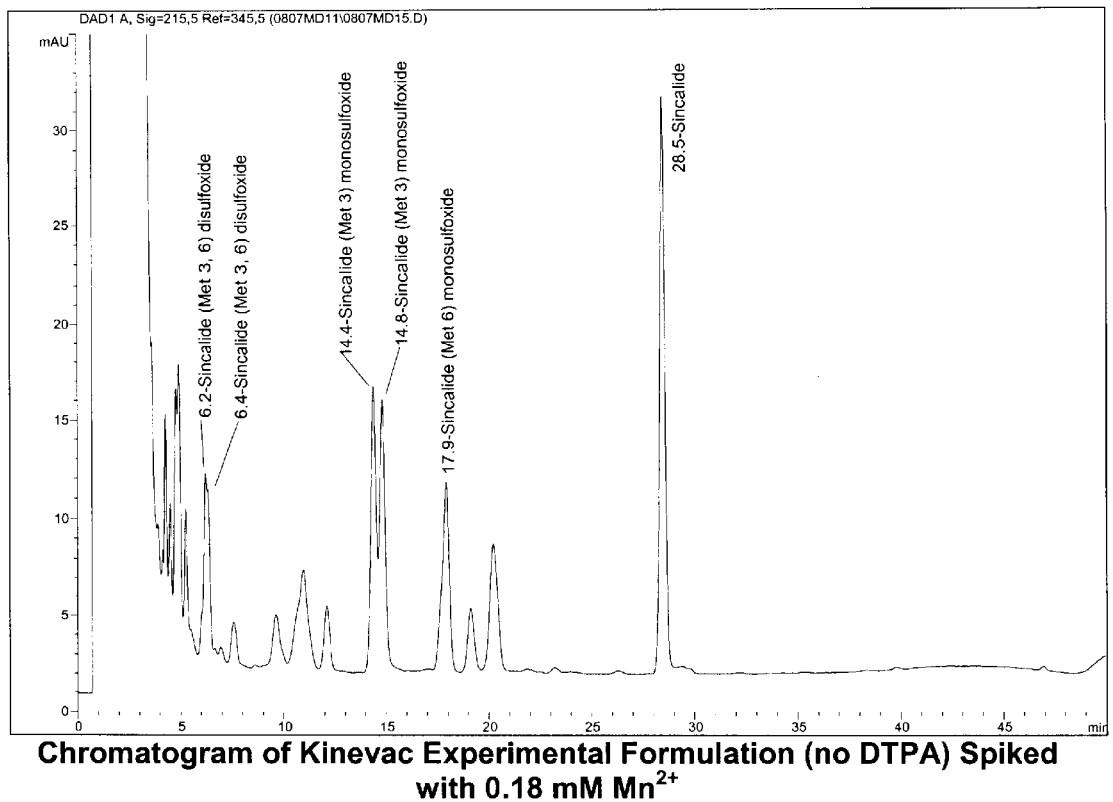
FIG. 10 is a chromatogram of KINEVAC® experimental formulation (no DTPA) spiked with 0.18 mM $Mn^{2+}$.
Figure 11:
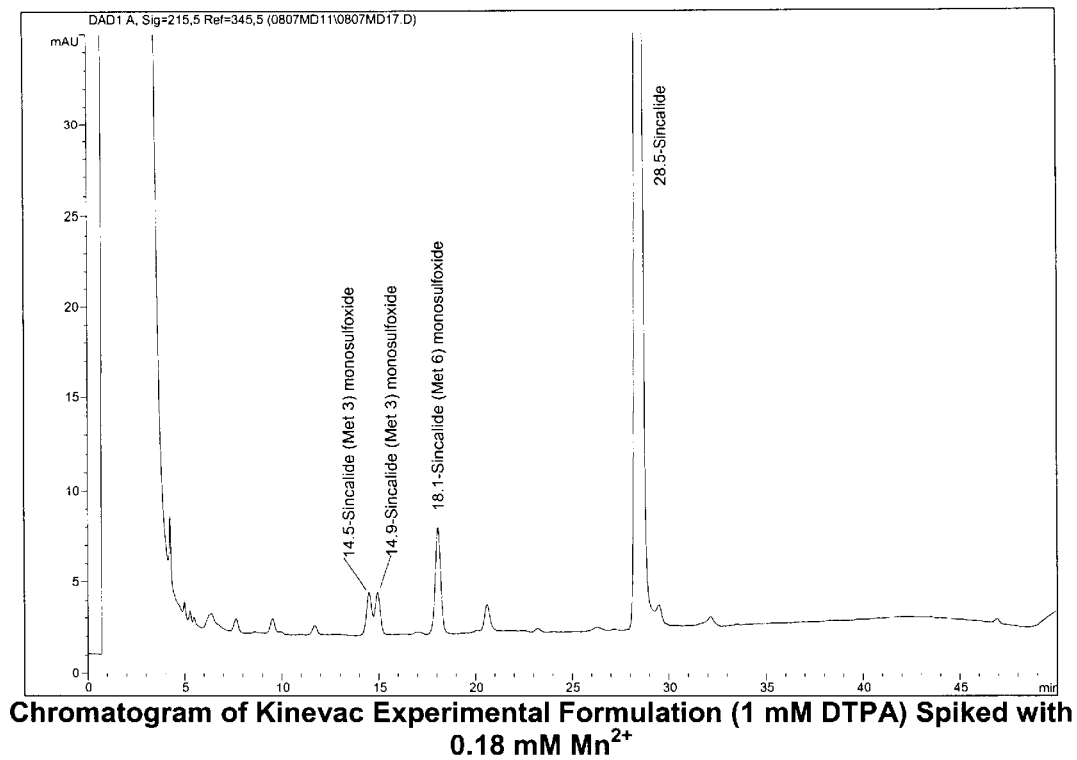
FIG. 11 is a chromatogram of KINEVAC® experimental formulation (1 mM DTPA) spiked with 0.18 mM $Mn^{2+}$.

The metal-containing solutions were analyzed within 8 hours for sincalide and related oxidized forms by RP-HPLC with gradient elution and UV detection at 215 nm, as described above. FIG. 7 shows the effects of the nine metals in the presence and absence of DTPA on the formation of sulfoxides (Met 3 and Met 6). These data show that, with the exception of $Cr^{3+}$, the amounts of sincalide Met 3 and Met 6 monosulfoxides increase in the presence of certain metals and in the absence of DTPA, while the presence of DPTA has an inhibitory effect on the formation of sincalide Met 3 and Met 6 monosulfoxides. Copper and manganese, in the absence of DTPA, have the greatest oxidative effect on the methionine residues of sincalide resulting in combined weight percentages of Met 3 and Met 6 monosulfoxides (vs sincalide) of 85.5 and 128.9, respectively. In addition to the presence of sincalide Met 3 and Met 6 monosulfoxides ($t_R$≈14.8 min. {doublet} and $t_R$≈18 min.), formation of sincalide disulfoxide ($t_R$≈6.5 min.) was also noted in the cases of copper and manganese, but not with the other metals.

Chromatograms of formulations spiked with copper or manganese (FIGS. 8–11) and with or without DTPA also support this conclusion. The analyses of the chromatographic profiles indicate that levels of DTPA at 1 mM (0.39 mg DTPA/mL) protect sincalide from metal-catalyzed oxidation to sulfoxides. As trace metals often arise in formulations as a result of excipient impurities and/or stopper extractables, the results of the study support the use of pentetic acid (DTPA) as a formulation excipient to chelate trace levels of free metals, thus reducing the formation of sincalide methionine mono- and disulfoxides and inhibiting the degradation of sincalide in solution. Sincalide formulations were prepared containing 2 mg DTPA/vial, equivalent to 1 mM upon reconstitution with 5 mL.

EXAMPLE 3

Effect of Surfactants on Sincalide Formulations

During the preliminary developmental studies of a new formulation that consisted of bulking agent/tonicity adjuster, buffer, salt, chelator, and sincalide, it was observed by HPLC analysis that the recovery of the active pharmaceutical ingredient, sincalide, in the bulk solution was sensitive to standing open to air. For example, when using reversed-phase gradient elution HPLC with UV detection at 215 nm to monitor sincalide potency, a substantial decrease of 50–60% in sincalide recovery was observed in unstoppered vials with a 2-mL fill of bulk solution either stirred or left standing open to air for 17 hours. Although to some extent, this sincalide decrease can be accounted for by an increase in the presence of sincalide mono- and disulfoxide degradants, these represent only a very minor percentage of the decreases noted. Thus the decrease in recovery is thought to be attributed to either adsorption/denaturing or air/liquid interface effects. To minimize sincalide degradation associated with surface adsorption, surfactants are added as formulation excipients in bulk and lyophilized formulations of sincalide.

Sincalide formulations consisting of a bulking agent/tonicity adjuster (D-mannitol), buffer (mono- and dibasic potassium phosphate), salt (sodium/potassium chloride) for tonicity, chelator (pentetic acid), and active ingredient (sincalide) were prepared using varying concentrations of the nonionic surfactant, polysorbate 80 (TWEEN® 80). Bulk solution and reconstituted lyophilized samples were either stoppered immediately or left unstoppered for 17 hours, and were assayed for sincalide recovery by reversed-phase gradient elution HPLC at 215 nm.

As shown in Table 8, the effect of TWEEN® 80 is more apparent in formulations that have been exposed to air. For bulk and reconstituted lyophilized formulations, the data show decreases in sincalide recovery of ≈50% and ≈20%, respectively, when compared to corresponding formulations containing a TWEEN® 80 concentration of 1 mg/mL. Low sincalide recoveries in closed bulk and reconstituted lyophilized formulations without TWEEN® 80 are also evident, but not nearly as substantial (4–8%) as the exposed formulations. These preliminary screening studies on the influence of TWEEN® 80 concentration indicate that <1 mg/mL bulk may be optimal.

TABLE 8

Sincalide Recovery in Formulations With and Without TWEEN ® 80

| Formulation Description (mg/mL Bulk) | Test Condition | TWEEN ® 80 Conc. (mg/mL) | Sincalide % Recovery |
|---|---|---|---|
| D-Mannitol (75.0), KH$_2$PO$_4$ (3.25), K$_2$HPO$_4$ (1.0), NaCl (5.0), DTPA (1.0), Sincalide (0.0025) TWEEN ® 80 (0; 0.1; 1.0) | Bulk; open (~17 h) | 1.0 | 97.0 |
| | | 0.0 | 47.0 |
| | Bulk; closed | 1.0 | 100.0 |
| | | 0.0 | 96.0 |
| | Lyophilized; open (~17h) | 1.0 | 91.3 |
| | | 0.1 | 98.2 |
| | | 0.01 | 98.3 |
| | | 0.0 | 78.4 |
| | Lyophilized; closed | 1.0 | 90.2 |
| | | 0.1 | 98.1 |
| | | 0.01 | 97.8 |
| | | 0.0 | 92.3 |

To compare the effects of two nonionic surfactants, sincalide formulations (75 mg/mL D-mannitol, 6.0 mg/mL KCl, 3.25 mg/mL KH$_2$PO$_4$, 1.0 mg/mL K$_2$HPO$_4$, 1.0 mg/mL DTPA, 0.0025 mg/mL sincalide (Bulk formulation)) were prepared using either TWEEN® 20 or TWEEN® 80 in varying amounts. The results of this experiment are presented in Table 9.

TABLE 9

Effect of Surfactants on Sincalide Recovery

| Sincalide Formulation | TWEEN ® Concentration (μg/mL Bulk) | Sincalide Recovery (%) |
|---|---|---|
| TWEEN ® 80 | | |
| A | 7.5 | 95.4 |
| B | 5.0 | 96.3 |
| C | 2.5 | 98.6 |
| G | 0 | 94.1 |
| TWEEN ® 20 | | |
| D | 7.5 | 99.5 |
| E | 5.0 | 101.3 |
| F | 2.5 | 98.7 |
| G | 0 | 94.1 |

As shown in Table 9, the data indicate that the presence of trace levels (2.5–7.5 μg/mL) of either TWEEN® 80 or TWEEN® 20 has a beneficial effect on the recovery of sincalide, when compared to formulations without surfactant. However, the sincalide recoveries (98–102%) with formulations containing TWEEN® 20 are consistently higher than recoveries (95–98%) with TWEEN® 80, and thus TWEEN® 20 is a preferred surfactant.

An additional experiment was performed to confirm the effect of the concentration of TWEEN® 20 in terms of sincalide recovery in both air exposed and sealed bulk formulation. Sincalide recovery, determined for bulk formulation (75.0 mg/mL D-mannitol, 6.0 mg/mL KCl, 3.25 mg/mL $KH_2PO_4$, 1.0 mg/mL DTPA, 0.0025 mg/mL sincalide) containing varying trace levels of TWEEN® 20 stored in open or closed vials using reversed-phase gradient elution HPLC, is shown in Table 10.

TABLE 10

Effect of TWEEN ® 20 Concentration on Recovery of Sincalide in Bulk Formations

| Sincalide Formulation | TWEEN ® 20 Concentration (μg/mL Bulk) | Sincalide % Recovery | |
|---|---|---|---|
| | | Open Vial | Closed Vial |
| D | 7.5 | 100.7 | 100.8 |
| E | 5.0 | 100.0 | 100.4 |
| F | 2.5 | 99.0 | 98.2 |
| G | 0 | 89.8 | 96.1 |

As shown in Table 10, the bulk formulations containing TWEEN® 20 have improved sincalide recoveries over formulations with no TWEEN® 20 and the sincalide recoveries are independent of the TWEEN® 20 concentration range (2.5–7.5 μg/mL bulk) studied. In addition, the air sensitivity relative to sincalide recovery was eliminated, as both open and closed formulations containing TWEEN® 20 have equivalent sincalide recoveries. Although these data support the use of TWEEN® 20, it was noted that 2-mL filled vials containing a TWEEN® 20 concentration of 5 μg/mL show slight foaming in the reconstituted product upon vigorous stirring. To reduce foaming, a lower TWEEN® 20 concentration was evaluated.

As summarized in Table 11, an experiment was conducted on the lyophilized product comparing the recovery of the sincalide in the formulations with TWEEN® 20 (2.5 ng/mL) and without TWEEN® 20. In this Example and the subsequent Examples, mannitol refers to D-mannitol, methionine refers to L-methionine, arginine refers to L-arginine monohydrochloride, and lysine refers to L-lysine monohydrochloride.

TABLE 11

Sincalide Recovery in Reconstituted Formulations With and Without TWEEN ® 20

| Formulation Description (mg/mL Bulk) | Sincalide % Recovery TWEEN ® 20 Concentration | |
|---|---|---|
| | 0 ng/nl | 2.5 ng/mL |
| Mannitol (85.0), | 94.8 (n = 5) | |
| $KH_2PO_4$ (4.5), | | 100.0 (n = 2) |
| DTPA (1.0), | | 100.0 (n = 2) |
| Methionine (2.0), | | 100.0 (n = 2) |
| Lysine (7.5), | | 99.0 (n = 2) |
| Arginine (15.0), | | |
| Sodium metabisulfite (0.02), | | |
| Sincalide (0.0025) | | |
| Average | 94.8 | 99.7 |
| Variance | 0.862 | 0.667 |
| P (T <= t) two-tail | $1.6 \times 10^{-5}$ | |

Reducing the amount of TWEEN® 20 to a minimal trace concentration (2.5 ng/mL) still produced a significant effect on the air/liquid interface and eliminated the foaming in the formulation. A statistical two-tail t-test performed on the results showed a significant difference (P<0.05) between 2.5 ng/mL and no TWEEN® 20 in the formulation. Based on these data, the effectiveness of TWEEN® 20, polyoxyethylene sorbitan monolaurate, as a surfactant was established by enhancing the sincalide recovery and thus maintaining sincalide potency in the formulation. A preferred formulation of sincalide includes the nonionic surfactant TWEEN® 20 as a trace excipient at a concentration of 2.5 ng/mL of bulk formulation equivalent to 1 ng/mL in the final product when reconstituted to 5 mL.

EXAMPLE 4

Effect of Antioxidants on Sincalide Formulations

An experiment was performed to evaluate the addition of antioxidants as stabilizing agents to prevent sincalide oxidation in formulations of sincalide (formulations for Example 4 contained 85 mg/mL mannitol, 0.005 mg/mL TWEEN® 20, 2.75 mg/mL $KH_2PO_4$, 1.0 mg/mL DTPA, 2.0 mg/mL methionine, 7.5 mg/mL lysine, 15 mg/mL arginine, 0.0025 mg/mL sincalide (Bulk formulation), except placebos which contained no sincalide.) The formation of sincalide methionine (Met 3 or Met 6) monosulfoxides, desulfated sincalide and unknown degradants was investigated. The effectiveness of sodium metabisulfite, ascorbic acid, cysteine, glutathione, sodium sulfate, benzalkonium chloride, and benzethonium chloride in inhibiting the degradation of sincalide in terms of their effect on sincalide recovery and sincalide-related impurities, was evaluated by HPLC.

The effect of various antioxidants on the stabilization of sincalide was evaluated on open and sealed sincalide formulations over 15 hours. The antioxidants were separately added at a concentration of 10 µg/mL to water-reconstituted lyophilized sincalide formulations containing all formulation ingredients except antioxidant. Spiked and unspiked solutions were pooled, subdivided, and either exposed to or protected from air over 15 hours. The sincalide and total sincalide-related impurities were monitored by reversed-phase HPLC with gradient elution and UV detection at 215 nm to compare the effectiveness of the antioxidants.

As shown in Table 12, the data at these concentrations indicate that benzalkonium chloride and benzethonium chloride had a significant destabilizing effect on sincalide, while ascorbic acid, cysteine, glutathione, and sodium sulfate were essentially equivalent to the control formulation (no antioxidant). Of all the sincalide formulation/antioxidant combinations examined, the formulation with 10 µg sodium metabisulfite/mL showed the highest sincalide potency (98.3%) over 8 hours, and the lowest total sincalide-related impurities (1.79%) through 15 hours. Therefore, sodium metabisulfite is a preferred antioxidant for formulations of the invention.

TABLE 14

Effect of Sodium Metabisulfite Concentration on Sincalide Oxidation

| Formulation | Sodium Metabisulfite Concentration (µg/vial) | % (Met 6) Monosulfoxide | | % Sincalide | |
|---|---|---|---|---|---|
| | | Un-stressed | Stressed (65° C., 64 h) | Un-stressed | Stressed (65° C., 64 h) |
| 1 | 0 | 0.08 | 0.20 | 95.7 | 95.1 |
| 2 | 10 | 0.07 | 0.09 | 95.1 | 96.0 |
| 3 | 30 | 0.07 | 0.10 | 95.0 | 96.9 |
| 4 | 60 | 0.06 | 0.08 | 95.8 | 96.2 |

The addition of sodium metabisulfite up to 60 µg/vial improved sinealide recovery and inhibited the oxidation of sincalide to the (Met 6) monosulfoxide derivative under stressed conditions. Based on this data, as there was no apparent concentration relationship, 40 µg/vial sodium metabisulfite was selected as the preferred concentration for the final formulation, using 30 µg/vial and 60 µg/vial as lower and upper limits, respectively.

TABLE 12

Effect of Various Antioxidants (10 µg/mL) on Sincalide Formulation Stability

| Antioxidant (10 µg/mL) | % Sincalide | | | | | | % Total Sincalide-Related Impurities | | | | | |
|---|---|---|---|---|---|---|---|---|---|---|---|---|
| | Sealed | | | Open | | | Sealed | | | Open | | |
| | 0 h | 7 h | 14 h | 1 h | 8 h | 15 h | 0 h | 7 h | 14 h | 1 h | 8 h | 15 h |
| Control (None) | 98.1 | 98.1 | 98.1 | 98.1 | 98.2 | 98.2 | 1.94 | 1.95 | 1.86 | 1.90 | 1.85 | 1.81 |
| Sodium Metabisulfite | 98.3 | 98.3 | 98.3 | 98.2 | 98.3 | 98.2 | 1.67 | 1.66 | 1.73 | 1.76 | 1.69 | 1.79 |
| Ascorbic Acid | 98.1 | 98.0 | 97.8 | 98.0 | 98.0 | 97.8 | 1.95 | 2.05 | 2.25 | 2.00 | 2.01 | 2.16 |
| Cysteine | 98.2 | 98.1 | 98.1 | 97.8 | 97.7 | 98.0 | 1.85 | 1.87 | 1.91 | 2.20 | 2.32 | 2.05 |
| Glutathione | 98.1 | 98.3 | 98.2 | 98.1 | 98.2 | 97.9 | 1.90 | 1.74 | 1.82 | 1.94 | 1.85 | 2.13 |
| Sodium Sulfate | 98.2 | 98.1 | 98.2 | 98.3 | 98.2 | 98.1 | 1.76 | 1.90 | 1.81 | 1.70 | 1.78 | 1.92 |
| Benzalkonium Chloride | 97.8 | 97.7 | 97.4 | 82.7 | 88.4 | 82.9 | 2.21 | 2.34 | 2.58 | 17.3 | 11.6 | 17.1 |
| Benzethonium Chloride | 97.9 | 98.0 | 98.0 | 92.1 | 88.0 | 92.6 | 2.13 | 1.98 | 1.96 | 7.93 | 12.0 | 7.36 |

To optimize the level of sodium metabisulfite in the formulation, lyophilized sincalide formulations were prepared containing four levels of sodium metabisulfite (0, 10, 30, and 60 µg/vial), as summarized in Table 13. Samples at each concentration were maintained under unstressed and stressed (65° C., 64 hours) storage conditions, and were subsequently assayed by HPLC. The "% sincalide" was determined, and the "% (Met 6) monosulfoxide" ($t_R \approx 19.7$ min.) was monitored as an indication of sincalide oxidation. The data are presented in Table 14.

TABLE 13

Sincalide Lyophilized Formulations

| Formulation No. | Fonnulation Description |
|---|---|
| 1 | complete formulation, no sodium metabisulfite |
| 2 | complete formulation, 10 µg sodium metabisulfite/vial |
| 3 | complete formulation, 30 µg sodium metabisulfite/vial |
| 4 | complete formulation, 60 µg sodium metabisulfite/vial |
| 5 | placebo(no sincalide), 40 ug sodium metabisulfite/vial |
| 6 | complete formulation, no sodium metabisulfite |
| 7 | complete formulation, 40 µg sodium metabisulfite/vial |

Another experiment was conducted under longer-term accelerated storage conditions utilizing a sincalide formulation with the optimized concentration (40 µg/vial) of sodium metabisulfite to confirm the protective effect on the degradation of sincalide. Sincalide lyophilized formulations with and without the antioxidant from the same batch were heat-stressed at 40° C. and 60° C. for 6 weeks. Also, formulations without sincalide from the same batch were heat-stressed at 40° C. for 8 months. The results of the HPLC analyses for % sincalide and % total impurity are presented in Table 15.

TABLE 15

Effect of Sodium Metabisulfite on Heat Stress-Related Impurities

| Formulation | Sodium Metabisulfite Concentration (µg/vial) | Storage Temp. (6 weeks) | % Sincalide | % Total Impurity |
|---|---|---|---|---|
| 7 | 40 | 40° C. | 96.7 | 3.30 |
| 6 | 0 | 40° C. | 93.4 | 6.56 |

TABLE 15-continued

Effect of Sodium Metabisulfite on Heat Stress-Related Impurities

| Formulation | Sodium Metabisulfite Concentration (μg/vial) | Storage Temp. (6 weeks) | % Sincalide | % Total Impurity |
| --- | --- | --- | --- | --- |
| 7 | 40 | 60° C. | 89.5 | 10.51 |
| 6 | 0 | 60° C. | 84.0 | 16.00 |

The results of this longer-term accelerated storage experiment further emphasized the need for the presence of the excipient sodium metabisulfite. Sincalide formulations with sodium metabisulfite (40 μg/vial) protected against sincalide heat stress-related degradant formation (3.30%), as compared without the antioxidant, which exhibited several elevated sincalide heat stress-related impurities (6.56%). These impurities were confirmed to be sincalide heat stress-related ($t_R \approx 35$ to 44 min.), as they were not present in chromatograms of formulations without sincalide. Sodium metabisulfite was chosen as a preferred antioxidant and stabilizing agent over ascorbic acid, cysteine, glutathione, sodium sulfate, benzalkonium chloride, and benzethonium chloride because it provided superior protection in inhibiting the oxidative and heat stress-related degradation of sincalide. A preferred concentration in the lyophilized formulation is 40 μg sodium metabisulfite/vial or 8 μg/mL in the reconstituted product.

EXAMPLE 5

Selection of Bulking Agent/Tonicity Adjuster

Due to the minute amount of the active pharmaceutical ingredient (API), sincalide (5 μg/vial), in the formulations of the invention, the use of a bulking agent was considered extremely beneficial for providing tonicity as well as for providing both structure and support for the API. Experiments were conducted for the selection and optimization of bulking agent in the sincalide formulations of the invention. Criteria for evaluation were: an efficient lyophilization cycle, a pharmaceutically elegant finished product, enhanced product solubility and usefulness as an excipient for isotonicity in the reconstituted product. Various concentrations of lactose, lactose/sodium chloride and mannitol were considered, and experimental batches containing these excipients were evaluated in terms of cake appearance, osmolality, dissolution rate, and thermal analysis including freeze dry microscopy, and electrical resistance vs. temperature measurements.

Experimental Formulations

Batch A: ingredients: lactose 375 mg/vial, dibasic sodium phosphate 12.0 mg/vial, DTPA 2.0 mg/vial, monobasic sodium phosphate 19.5 mg/vial , and 0.005 mg/vial sincalide.

Batch $C_{1-3}$: ingredients: mannitol 170 mg/vial, dibasic potassium phosphate 9.0 mg/vial, TWEEN® 20<0.01 mg/vial, methionine 4.0 mg/vial, lysine 15.0 mg/vial, arginine 30.0 mg/vial, sodium metabisulfite 0.04 mg/vial, sincalide 0.005 mg/vial, and DTPA 2.0 mg/vial.

Batch $D_1$: ingredients: lactose 150 mg/vial, dibasic potassium phosphate 9.1 mg/vial, DTPA 2.0 mg/vial, monobasic sodium phosphate 9.8 mg/vial, and NaCl 21.0 mg/vial.

Batch $E_1$: ingredients: lactose 200 mg/vial, dibasic sodium phosphate 7.5 mg/vial, DTPA 2.0 mg/vial and NaCl 17 mg/vial.

Batch $F_{1-2}$:

$F_1$: ingredients: mannitol 250 mg/vial, dibasic sodium phosphate 7.5 mg/vial, DTPA 2.0 mg/vial and sincalide 0 mg/vial; and $F_2$: ingredients: mannitol 206 mg/vial, dibasic sodium phosphate 7.5 mg/vial, DTPA 2.0 mg/vial and sincalide 0.005 mg/vial.

Batch $H_{1-2}$:

$H_1$: ingredients: mannitol 180 mg/vial, dibasic sodium phosphate 6.0 mg/vial, sincalide 0 mg/vial, NaCl 5 mg/vial and DTPA 2.0 mg/vial; and $H_2$: ingredients: mannitol 150 mg/vial, dibasic potassium phosphate 4.5 mg/vial, sincalide 0.005 mg/vial, NaCl 10 mg/vial and DTPA 2.0 mg/vial.

Batch $I_{1-2}$:

$I_1$: ingredients: mannitol 140 mg/vial, dibasic potassium phosphate 5.5 mg/vial, TWEEN® 20 0.01 mg/vial, methionine 4.0 mg/vial, lysine 60.0 mg/ vial, sincalide 0.005 mg/vial and DTPA 2.0 mg/vial; and $I_2$: ingredients: mannitol 170 mg/vial, dibasic potassium phosphate 5.5 mg/vial, TWEEN® 20 0.01 mg/vial, methionine 4.0 mg/vial, lysine 30.0 mg/vial, sincalide 0.005 mg/vial and DTPA 2.0 mg/vial.

Batch J: ingredients: mannitol 170 mg/vial, dibasic potassium phosphate 8.5 mg/vial, TWEEN® 20 0.01 mg/vial, methionine 4.0 mg/vial, lysine 15.0 mg/vial, arginine 30.0 mg/vial, Na metabisulfite 0.04 mg/vial, sincalide and DTPA 2.0 mg/vial.

Methods:

1. Appearance: Visual assessment of the freeze-dried plug.
2. Osmolality: Determined by vapor pressure osmometry.
3. Dissolution: Dissolution time measured by visual inspection under an inspection light upon reconstitution with 5 mL of water.
4. Thermal Analysis:
   a. Electrical resistance vs. temperature measurements: Electrical resistance measured using a proprietary resistance instrument, temperature measured using a 32-gauge type T thermocouple.
   b. Freeze drying microscopy: Performed using a freeze dry microscope an Infinivar microscope and color camera.

In the initial investigations lactose was used as a bulking agent/tonicity adjuster. The formulation as listed in table 16 is based on a 3-mL fill volume with a high concentration of lactose to achieve isotonicity in the reconstituted product. The osmolality for this formulation upon reconstitution with 5 mL of water was ~300 mOsm/kg.

TABLE 16

Lactose Containing Sincalide Formulation (Batch A)

| Raw Materials | Function | Concentration (mg/vial) |
| --- | --- | --- |
| Lactose | Bulking Agent/Tonicity Adjuster | 375 |
| Dibasic Sodium Phosphate | Buffer | 12.0 |
| Monobasic Sodium Phosphate | Buffer | 19.5 |
| Pentetic Acid | Chelator | 2.0 |
| Sincalide | Active | 0.005 |

This experimental formulation, Batch A, with a lyophilization cycle of 130 hours (≈5.4 days) showed evidence of meltback in the lyophilized cakes and had reconstitution dissolution times of ≧9 minutes. The high number of vials with poor cake formation and the long freeze dry cycle required were attributed to the high concentration of lactose (125 mg/mL) in the bulk formulation relative to its solubility and the high fill volume (3-mL) in a small vial.

Studies were undertaken to reduce cycle time and improve product appearance/solubility by modifying the initial lactose formulation with the use of an additional excipient, sodium chloride, thereby reducing lactose concentration and the fill volume from 3 to 2-mL.

TABLE 17

Lactose/NaCl Containing Sincalide Formulations (Batches $D_1$ and $E_{1-2}$)

| Raw Materials | Function | Concentration (mg/vial) |
|---|---|---|
| Lactose | Bulking Agent/ Tonicity Adjuster | 150–200 |
| Dibasic Sodium Phosphate | Buffer | 12.0 |
| Monobasic Sodium Phosphate | Buffer | 19.5 |
| Pentetic Acid | Chelator | 2.0 |
| Sodium Chloride | Tonicity Adjuster | 17–21 |
| Sincalide | Active | 0.005 |

Use of NaCl contributed to the isotonicity of the product with osmolality values in the range of 240 to 270 mOsm/kg, while permitting a reduction in the concentration of lactose. Varying the amounts of lactose, sodium chloride and sodium phosphate decreased the lyophilization cycle from 130 hours to 96 hours, but did not consistently improve the appearance of the freeze-dried cake.

Thermal analysis of two experimental formulations with varying lactose/sodium chloride ratios (Table 18) confirm that the relatively long lyophilzation cycles for these formulations were due to low primary drying temperatures in the range of –38° C. to –42° C., resulting in slow sublimation rates at these temperatures. In addition to long lyophilization cycles, the low primary drying temperatures lead to increased vial-to-vial variation and an increased risk of poor plug appearance with associated solubility issues.

TABLE 18

Thermal Analysis of Experimental Lactose/NaCl Formulations

| Batch | Lactose/NaCl Concentration (mg/vial) | Freezing Temp. Range (° C.) | | Primary Drying Temp. Range (° C.) | |
|---|---|---|---|---|---|
| | | High | Low | High | Low |
| $D_1$ | 150/21 | –32 | –39 | –39 | –42 |
| $E_1$ | 200/17 | –15 | –35 | –36 | –38 |

Mannitol, a common excipient for freeze-dried pharmaceuticals, was selected next for evaluation as bulking agent because of the high melting temperature of the mannitol/ice eutectic mixture (about –1.5° C.) and its tendency to crystallize from frozen aqueous solutions. Ideally, this leads to shorter primary and secondary drying times, promoting an efficient freeze-drying cycle and a physically stable, pharmaceutically elegant freeze-dried solid. Several bench-scale batches were prepared, replacing lactose with D-mannitol while maintaining isotonicity with a 2 mL fill volume, to evaluate the parameters of cycle time and primary drying temperature and the solubility of the solid cake. The freeze dry cycle parameters along with lyophilized product reconstitution times with a 5 mL reconstitution volume are shown in Table 19.

TABLE 19

Effect of Formulation Bulking Agent/Tonicity Adjuster on Lyophilization Cycle Optimization and Reconstitution/Dissolution Time

| Batch | Formulation Description (mg/vial) | Bulking Agent (mg/vial) | Osmolality (mOsm/kg) | Freeze Dry Cycle Parameters | Dissolution Time (sec) |
|---|---|---|---|---|---|
| F1 | $Na_2HPO_4$ (7.5), DTPA (2.0) | Mannitol (250) | 280 | Total Cycle 85 hr Primary drying @ –34° C. | 12–48 (n = 10) |
| F2 | $Na_2HPO_4$ (7.5), DTPA (2.0) | Mannitol (206) | 240 | Total Cycle 69 hr Primary drying @ –25° C. | 22–71 (n = 30) |

Lyo-cycle time was reduced from >130 hours for lactose formulations, to ~69 hours for the mannitol formulation, Batch $F_2$. The cakes from both formulations, $F_1$ and $F_2$ dissolved in 5 mL of water in approximately the same time range of <1 minute. Increasing the primary drying temperature from ~–34° C. to –25° C. Batch $F_1$ vs. Batch $F_2$ had the desired effect of reducing the overall cycle time from 85 to 69 hours.

Additional studies were conducted to optimize the mannitol concentration and lyo-cycle time for a 2-mL fill volume. These studies were carried out concurrently with formulation development studies to adjust the osmolality to ~250 mOsm/Kg after reconstitution and to stabilize the peptide by addition of other excipients to the formulation (Table 20).

TABLE 20

The Effect of Mannitol Concentration on Appearance, Solubility and Freeze Dry Cycle of Sincalide Formulations

| Batch | Formulation Description (mg/vial) | Bulking Agent (mg/vial) | Osmolality (mOsm/kg) | Freeze Dry Cycle Parameters | Moisture Content (%) | Appearance/ Dissolution Time (sec) |
|---|---|---|---|---|---|---|
| $H_1$ | $Na_2HPO_4$ (6.0), DTPA (2.0), Sincalide (0) | Mannitol (180) NaCl (5.0) | 250 | Total Cycle: 36 hr 27 hr primary @ –8° C. | ND | Solid cake/ 22–66 (n = 30) |

TABLE 20-continued

The Effect of Mannitol Concentration on Appearance, Solubility and Freeze Dry Cycle of Sincalide Formulations

| Batch | Formulation Description (mg/vial) | Bulking Agent (mg/vial) | Osmolality (mOsm/kg) | Freeze Dry Cycle Parameters | Moisture Content (%) | Appearance/ Dissolution Time (sec) |
|---|---|---|---|---|---|---|
| $H_2$ | $K_2HPO_4$ (4.5), DTPA (2.0), Sincalide (0.005) | Mannitol (150) NaCl (10.0) | 240 | Total Cycle: 30 hr 23 hr primary @ $-10°$ C. | 1 | Solid cake/ 11–31 (n = 30) |
| $I_1$ | TWEEN® (0.01), $K_2HPO_4$ (5.5), Methionine (4.0), Lysine (60.0), DTPA (2.0), Sincalide (0.005) | Mannitol (140) | 250 | Total Cycle: 59 hr 50 hr primary @ $-22°$ C. | 1 | Solid cake/ 21–69 (n = 5) |
| $I_2$ | TWEEN® (0.01), $K_2HPO_4$ (5.5), Methionine (4.0), Lysine (30.0), DTPA (2.0), Sincalide (0.005) | Mannitol (170) | 250 | Total Cycle: 33 hr 26 hr primary @ $-12°$ C. | 1 | Solid cake/ 8–15 (n = 5) |

ND = Not Determined

These results demonstrate that an increase in primary drying temperature from ~$-25°$ C. to the $-8$ to $-12°$ C. range significantly reduced cycle times from 69 to 30 hours and produced solid dry cakes that reconstitute within 1 minute.

Additional optimization studies designed to enhance the long term stability of sincalide resulted in a preferred sincalide formulation of 170 mg of D-mannitol/vial with the additional excipients (in mg/vial): TWEEN® 20 (0.01), $K_2HPO_4$ (8.5), methionine (4.0), lysine (15.0), arginine (30.0), DTPA (2.0), and sodium metabisulfite (0.04). The osmolality of this optimized formulation was approximately 300 mOsm/kg when reconstituted with 5 mL of water. Thermal analysis of this formulation using freeze-dry microscopy and electrical resistance vs. temperature measurements, indicated an upper limit for product primary drying temperature of $-13°$ C. to $-15°$ C. to achieve acceptable product quality.

To confirm all findings, three scale-up pilot batches, $C_{1-3}$, of a preferred sincalide formulation, in a fill volume of 2 mL/vial, were prepared and freeze dried in full-scale production driers to prove process transferability from development equipment to production equipment. The drying cycle for these batches incorporated a primary drying temperature of $-12°$ C.$\pm 3°$ C. and an overall cycle time of 53–61 hours (Table 21).

TABLE 21

Operating Parameters and Final Product Performance of Scale-up Pilot Batches Prepared with Mannitol as a Bulking Agent

| | Lyophilization | | | | | |
|---|---|---|---|---|---|---|
| Batch | Primary Temp (° C.) | Total Cycle Time (Hrs) | Osmolality (mOsm/kg) | Plug Appearance | Moisture Content % | Dissolution Time (sec) |
| $C_1$ | $-12$ | 58 | 300 | Solid cake | 1 | 10 |
| $C_2$ | $-12$ | 53 | 300 | Solid cake | 1 | 10 |
| $C_3$ | $-12$ | 61 | 300 | Solid cake | 1 | 10 |

The data from these studies support the selection of mannitol as a particularly preferred bulking agent, preferably in an amount of about 170 mg/vial. Using this concentration, the freeze dry cycle is 53–61 hours when filled as a 2-mL fill. The finished product is a pharmaceutically elegant, solid white cake, which is reconstituted within one minute using 5 mL of water, resulting in a solution with an osmolality of ~300 mOsm/Kg.

EXAMPLE 6

Effect of Amino Acids on Sincalide Formulations

During formulation studies it was observed that both exposure to air and lyophilization were areas of concern for scale-up manufacturing due to reduced potency of sincalide in the formulation. The reduced potency was a result of surface adsorption/denaturation resulting from exposure of sincalide to air, and yielding degradants via oxidation. Exposure of sincalide formulations to thermal stress during lyophilization also resulted in degradation and reduced recovery of sincalide.

Experiments were conducted to evaluate several amino acids as potential stabilizers of sincalide, including the non-polar (hydrophobic) methionine residue, aspartic acid and glutamic acid, the polar glycine and cysteine residues, and the basic lysine and arginine amino acids.

Except as otherwise indicated, the formulations used in this example for testing the efficacy of various amino acids contained the following ingredients (bulk): 75.0 mg/mL mannitol; 3.25 mg/mL $KH_2PO_4$; 1.0 mg/mL $K_2HPO_4$; 1.0 mg/mL pentetic acid (DTPA); 5.0 mg/mL NaCl; and the active peptide, sincalide (0.0025 mg/mL). Initially, the non-polar amino acid L-methionine was evaluated for the reformulation since methionine residues can act as endogenous antioxidants, or as scavengers by reacting with hydroxyl free radicals and other reactive oxygen species. Thus, methionine could improve the processing stability of sincalide formulations by providing a protectant or antioxidant effect for sincalide and being preferentially oxidized. Table 22 below summarizes the results obtained during exposure of experimental formulations to air when various amounts of L-methionine were added to a formulation containing mannitol, sodium chloride, potassium phosphate, and pentetic acid. For these experiments, liquid formulations in open and closed vials were used to simulate processing of the product. For formulation in open vials, the recovery of sincalide was improved approximately 60% and the concentration of sincalide-related impurities decreased as the level of methionine was increased from 0.0 to 2.0 mg/mL in the bulk formulation.

TABLE 22

Evaluation of Methionine as a Processing Stabilizer for Bulk Formulations - Open vs Closed Vials.

| L-Methionine | Sincalide Recovery (%) | | Related Impurities (%) | |
|---|---|---|---|---|
| (mg/mL Bulk) | Open | Closed | Open | Closed |
| 2.0 | 75.5 | 95.7 | 15.0 | 0.7 |
| 0.50 | 64.7 | 94.8 | 19.3 | 0.8 |
| 0.025 | 35.7 | 93.9 | 35.9 | 1.0 |
| 0.00 | 13.9 | 95.7 | 52.7 | 1.3 |

For comparison to the non-polar amino acid methionine as a potential processing stabilizer, polar amino acids such as glycine and cysteine were also evaluated. Formulations containing these amino acids were exposed to air in open vials and compared to product in closed vials. The efficacy of these amino acids, in terms of sincalide recovery and sincalide-related impurities, was compared to the improvements previously observed for the liquid formulation in the presence of methionine. Table 23 presents the sincalide recoveries for experimental formulations containing variable concentrations of methionine, cysteine or glycine.

TABLE 23

Comparison of Methionine, Glycine and Cysteine as Processing Stabilizers for Bulk Formulations - Open vs. Closed Vials

| Amino Acid | | Sincalide Recovery (%) | | Related impurities (%) | |
|---|---|---|---|---|---|
| (mg/mL Bulk) | | Open | Closed | Open | Closed |
| L-Cysteine | 2.0 | 50.0 | 96.0 | 31.0 | 1.0 |
| L-Methionine | 2.5 | 82.4 | 97.4 | 10.5 | 0.7 |
| L-Methionine | 2.0 | 89.9 | 97.7 | 6.4 | 0.7 |
| None | 0 | 37.0 | 96.0 | 35.0 | 1.6 |
| L-Glycine | 2.5 | 31.9 | 93.2 | 44.9 | 1.6 |
| L-Glycine | 2.0 | 22.3 | 92.5 | 51.1 | 1.1 |

Results demonstrated that addition of either cysteine or glycine to a bulk formulation containing mannitol, potassium phosphate, sodium chloride and pentetic acid did not show a significant effect in either reduced levels of sincalide impurities or improved recovery of sincalide when formulations were exposed to air in open vials.

Lysine, a basic amino acid, was the next amino acid evaluated for use in sincalide formulations of the invention. As shown in Table 24, experimental formulations (70–85 mg/mL mannitol, 0.005 mg/mL TWEEN® 20, 2.75 mg/mL $KH_2PO_4$, 1.0 mg/mL DTPA, 2.0 mg/mL methionine, 0.0025 mg/mL sincalide) were prepared to contain varying concentrations of lysine and evaluated for sincalide recovery.

TABLE 24

Evaluation of Lysine as a Stabilizer in Sincalide Reconstituted Formulations

| | Sincalide Recovery (%) | | | | | |
|---|---|---|---|---|---|---|
| DL-Lysine | 1 Week | | 3 Weeks | | 5 Weeks | |
| (mg/mL Bulk) | 5° C. | 40° C. | 5° C. | 40° C. | 5° C. | 40° C. |
| 0.0 | 99.6 | 84.3 | 95.5 | 51.2 | NA | 25.4 |
| 5.0 | 98.1 | 95.4 | 93.6 | 98.4 | | 92.0 |
| 15.0 | 97.3 | 97.0 | 94.3 | 99.4 | | 93.2 |
| 30.0 | 96.6 | 95.0 | 95.5 | 97.2 | | 89.7 |

NA = Not Applicable

After accelerated storage, lyophilized formulations containing lysine resulted in significantly improved recoveries of sincalide compared to a lyophilized control formulation without lysine. Formulations containing lysine resulted in 50% and 75% improvements in sincalide recovery after 3 and 5 weeks storage at 40° C., respectively, demonstrating that lysine contributed to the stability of lyophilized formulations when subjected to thermal stress.

The improved sincalide recoveries observed in the presence of methionine and lysine suggested that other amino acids might also be suitable as bulk additives in the reformulation. Therefore, formulation studies continued with the evaluation of two acidic amino acids, aspartic acid and glutamic acid. Table 25 presents sincalide recoveries for experimental formulations (85.0 mg/mL mannitol, 0.005 mg/mL TWEEN® 20, 2.75 mg/mL $KH_2PO_4$, 1.0 mg/mL DTPA, 2.0 mg/mL methionine, 0.0025 mg/mL sincalide) containing the following amounts of either lysine, aspartic acid or glutamic acid.

TABLE 25

Comparison of Lysine, Aspartic Acid and Glutamic Acid as Stabilizers in Sincalide Reconstituted Formulations

| Formulation Process Conditions | ID | Amino Acid (mg/mL) | | Sincalide Recovery (%) | | |
|---|---|---|---|---|---|---|
| | | | | 0 Days | 10 Days | 30 Days |
| Liquid Bulk Stored 5° C. | A | DL-Lysine HCl | 15.0 | 99.9 | 98.4 | NA |
| | B | L-Aspartic Acid | 11.0 | 98.2 | 96.3 | |
| | C | L-Glutamic Acid | 12.0 | 97.3 | 96.3 | |
| Lyophilized Cake Stressed 40° C. | A | DL-Lysine HCl | 15.0 | NA | 98.2 | 99.1 |
| | B | L-Aspartic Acid | 11.0 | | 94.6 | 92.8 |
| | C | L-Glutamic Acid | 12.0 | | 95.5 | 95.7 |
| | E | Control | 0.0 | | 81.7 | 53.8 |

NA = Not Applicable

The results demonstrated that with increasing storage time at 40° C., lysine consistently provided better protection than either aspartic acid or glutamic acid. The results obtained for lysine also suggested that arginine, another basic amino acid, or potentially some combination of lysine and arginine, might further enhance protection during lyophilization and thermal stress. Experimental formulations (85.0 mg/mL mannitol, 0.005 mg/mL TWEEN® 20, 2.75 mg/mL $KH_2PO_4$, 1.0 mg/mL DTPA, 2.0 mg/mL methionine, 0.0025 mg/mL sincalide) were prepared to contain varying concentrations of lysine, arginine, or a combination of lysine and arginine and evaluated for sincalide recovery (Table 26).

TABLE 26

Evaluation of Lysine and Arginine as Stabilizers in Sincalide Reconstituted Formulations

| Amino Acid | | Sincalide Recovery (%) | |
|---|---|---|---|
| (mg/mL Bulk) | | 64 hrs. @ 65° C. | 1 week @ 40° C. |
| DL-Lysine | 15.0 | 88.4 | ND |
| L-Arginine | 17.5 | 93.0 | |
| DL-Lysine | 7.50 | 99.8 | |
| L-Arginine | 8.75 | | |
| DL-Lysine | 7.5 | 93.8 | 96.4 |
| L-Arginine | 17.5 | | |
| DL-Lysine | 5.0 | 91.2 | ND |
| L-Arginine | 11.7 | | |
| DL-Lysine | 7.5 | 95.1 | ND |
| L-Arginine | 15.0 | | |
| N/A (control) | 0.0 | 43.3 | ND |

NA = Not Applicable, ND = Not Determined

Results confirmed that after lyophilization and stressing for 64 hours @ 65° C., approximately 50–70% improvement in sincalide recovery was observed for formulations containing lysine, arginine, or a combination of the two. Formulations containing both lysine and arginine exhibited the highest sincalide recovery values, indicating that the combination of these two amino acids provided a particularly stabilizing effect under heat-stressed storage conditions. The mid-point combination of 7.5 mg/mL of lysine and 15.0 mg/mL of arginine afforded suitable protection for the lyophilized and heat-stressed product, resulting in sincalide recoveries of >95%.

Methionine, lysine and arginine are preferred over polar amino acids such as is glycine and cysteine and acidic amino acids such as aspartic acid and glutamic acid for use as stabilizers in the sincalide formulations of the invention. Methionine improved the processing stability of the formulation, resulting in improved recovery of sincalide, and the combination of lysine and arginine contributed to the stability of the product during lyophilization and heat-stressing, also resulting in improved recovery of sincalide. Preferred concentrations in lyophilized formulations of the invention are: methionine (4.0 mg/vial), lysine (15.0 mg/vial) and arginine (30.0 mg/vial).

EXAMPLE 7

Reconstituted Shelf-life Studies

A. In-Vial Post-Reconstitution Stability

Experiments were performed to determine the post-reconstitution stability of sincalide in terms of appearance, solubility, particulate matter, color, pH, sincalide assay, desulfated sincalide assay and other sincalide-related impurities through 8 hours at ambient temperature. Lyophilized vials from three 105-L scale-up pilot batches of sincalide formulations were reconstituted with 5.0 mL of purified water.

Testing was conducted at 0, 2, 4, 6, and 8 hours post-reconstitution for appearance, solubility, particulate matter, color, and pH. Testing was conducted on duplicate vials at 0, 4, and 8 hours post-reconstitution for sincalide assay, desulfated sincalide assay and other sincalide-related impurities using reversed-phase HPLC with gradient elution and UV detection at 215 nm.

The test results for appearance, solubility, particulate matter, color, and pH performed at 0, 2, 4, 6, and 8 hours post-reconstitution for the three sincalide formulation preparations are shown in Table 27.

TABLE 27

Post Reconstitution Test Results

| Preparation | Time (hr) | Appearance | Solubility (sec.) | Particulate Matter | Color | pH meter 1 | pH meter 2 |
|---|---|---|---|---|---|---|---|
| A | 0 | Clear | 20 | Complies | Colorless | 7.2 | 7.0 |
| | 2 | Clear | 20 | Complies | Colorless | 7.1 | 7.0 |
| | 4 | Clear | 20 | Complies | Colorless | 7.2 | 7.0 |
| | 6 | Clear | 20 | Complies | Colorless | 7.2 | 7.0 |
| | 8 | Clear | 20 | Complies | Colorless | 7.2 | 7.0 |
| B | 0 | Clear | 20 | Complies | Colorless | 7.2 | 7.0 |
| | 2 | Clear | 20 | Complies | Colorless | 7.1 | 7.0 |
| | 4 | Clear | 20 | Complies | Colorless | 7.2 | 7.0 |

TABLE 27-continued

Post Reconstitution Test Results

| Preparation | Time (hr) | Appearance | Solubility (sec.) | Particulate Matter | Color | pH meter 1 | pH meter 2 |
|---|---|---|---|---|---|---|---|
|  | 6 | Clear | 20 | Complies | Colorless | 7.1 | 7.0 |
|  | 8 | Clear | 20 | Complies | Colorless | 7.1 | 7.0 |
| C | 0 | Clear | 20 | Complies | Colorless | 7.1 | 7.0 |
|  | 2 | Clear | 20 | Complies | Colorless | 7.1 | 7.0 |
|  | 4 | Clear | 20 | Complies | Colorless | 7.1 | 7.0 |
|  | 6 | Clear | 20 | Complies | Colorless | 7.1 | 7.0 |
|  | 8 | Clear | 20 | Complies | Colorless | 7.1 | 7.0 |

For the three preparations examined (referred to herein as preparations A, B, and C), no changes were observed in the parameters tested and all results were within specifications through the 8-hour testing period (85 mg/mL mannitol; $2.5 \times 10^{-6}$ mg/mL TWEEN® 20; 4.5 mg/mL $KH_2PO_4$; 1.0 mg/mL DTPA, 0.02 mg/mL sodium metabisulfate, 2.0 mg/mL methionine, 7.5 mg/mL lysine, 15.0 mg/mL arginine, 0.0025 mg/mL sincalide (Bulk formulation). The HPLC test results for sincalide assay, desulfated sincalide assay and other sincalide-related impurities performed at 0, 4, and 8 hours post-reconstitution for the three formulation preparations are shown in Table 28.

TABLE 28

Post Reconstitution HPLC Test Results

| Preparation | Time (h) | Sincalide (µg/vial) | Desulfated Sincalide (w/w % sincalide) | Sincalide Related Impurities (% Impurity Index) |
|---|---|---|---|---|
| A | 0 | 4.99, 4.98 | 0.32, 0.33 | 1.41, 1.32 |
|  | 4 | 4.99, 4.97 | 0.32, 0.36 | 1.40, 1.35 |
|  | 8 | 4.97, 4.97 | 0.35, 0.39 | 1.40, 1.34 |
| B | 0 | 5.04, 5.04 | 0.28, 0.27 | 1.29, 1.37 |
|  | 4 | 5.04, 5.03 | 0.30, 0.29 | 1.30, I.39 |
|  | 8 | 5.03, 5.01 | 0.31, 0.31 | 1.44, 1.41 |
| C | 0 | 4.97, 4.94 | 0.36, 0.36 | 1.48, 1.33 |
|  | 4 | 4.97, 4.94 | 0.39, 0.37 | 1.41, 1.37 |
|  | 8 | 4.97, 4.92 | 0.44, 0.44 | 1.46, 1.41 |

All results were within specifications. The sincalide potency was unchanged over time. The desulfated sincalide and other sincalide-related impurities show only relatively minor increases which are insignificant with respect to their individual specifications of 2% and 5%, respectively. The study shows that the initial test values of reconstituted sicalide formulations are representative of results obtained throughout the 8-hour shelf life of reconstituted product. The data provided demonstrate the post-reconstitution stabilty of the formulation and support a post-reconstitution shelf-life of 8 hours under ambient conditions.

B. Post-Reconstitution Dilution Study

An experiment was performed to determine the stability of sincalide formulations of the present invention that have been reconstituted and diluted.

Duplicate vials from three 105-L batches of sincalide formulations of the invention were constituted with 5 mL water. Vial contents were quantitatively trasferred (using Sodium Chloride Injection USP to rinse) to 100-mL volumetric flasks and up to 8.4 mL of the formulations were diluted to volume (100 mL) with Sodium Chloride Injection USP. Sincalide potency, pH and visual appearance were tested 1-hour post preperation. The results of the testing are presented in Table 29.

TABLE 29

Results for Sincalide Formulations to 100 mL With 0.9% Saline at 1 Hour Post-Reconstitution

| Preparation | Sample No. | Sincalide Potency (µg/vial) | pH | Appearance | Color | Particulate Matter |
|---|---|---|---|---|---|---|
| A | 1 | 4.8 | 6.9 | Clear | Colorless | Free of particles |
|  | 2 | 5.0 | 6.9 | Clear | Colorless | Free of particles |
| B | 1 | 5.2 | 6.9 | Clear | Colorless | Free of particles |
|  | 2 | 4.9 | 6.8 | Clear | Colorless | Free of particles |
| C | 1 | 4.9 | 6.9 | Clear | Colorless | Free of particles |
|  | 2 | 4.9 | 6.8 | Clear | Colorless | Free of particles |
| Mean |  | 5.0 | 6.9 |  |  |  |
| Std. Dev. |  | 0.1 | 0.1 |  |  |  |
| Confidence Interval (p = 0.95 and 5 deg. Freedom) |  | 4.8–5.1 | 6.8–6.9 |  |  |  |
| CV (%) |  | 2.8 | 0.8 |  |  |  |

All sincalide potency, pH and appearance results for diluted samples (reconstituted vial contents further diluted to 100 mL) measured 1-hour post reconstitution were within the product specifications for the reconstituted product (vial reconstituted with 5 mL water).

EXAMPLE 8

Sincalide Specific Assay using HPLC

An HPLC method was developed and validated for the determination of sincalide potentcy, quatitation of desulfated sincalide impurity and determination of a sincalide-related impurity index in KINEVAC®. The method is suitable for determining the reconstituted stabiliity of KINEVAC® when reconstituted as per the product package insert. The reversed phase method employs a $C_{18}$ (5 µm, 300 Å) column, stepwise th mobile phase components consisting of 0.15% trifluoroacetic acid in water (solvent A) and 0.125% trifluoroacetic acid in acetonitrile (solvent B), and UV detection at 215 nm.

Figure 12:
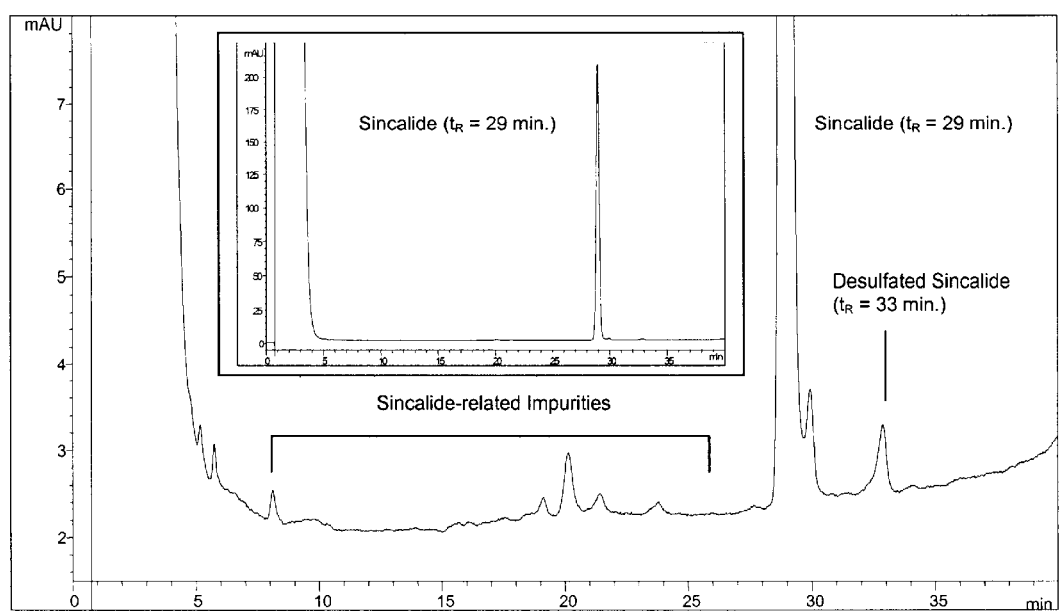
FIG. 12 shows representative full-scale and expanded scale chromatograms of a lyophilized reformulation of KINEVAC® upon reconstitution with 5 mL water, resulting in a sincalide concentration of 1 µg/mL.

FIG. 12 shows representative full-scale and expanded-scale chromatograms of a lyophilized reformulation of KINEVAC® upon reconstitution with 5 mL water, resulting in a sincalide concentration of 1 µg/mL.

Other Embodiments

Although the present invention has been described with reference to preferred embodiments, one skilled in the art can easily ascertain its essential characteristics, and without departing from the spirit and scope thereof can make various changes and, modifications of the invention to adapt it to various usages and conditions. Those skilled in the art will recognize or be able to ascertain using no more than routine experimentation, many equivalents to the specific embodiments of the invention described herein. Such equivalents are encompassed by the scope of the present invention.

All publications, patents, and applications mentioned in this specification are herein incorporated by reference.

We claim:

1. A stabilized, physiologically acceptable formulation of sincalide comprising:
    (a) an effective amount of sincalide,
    (b) at least one stabilizer,
    (c) a surfactant/solubilizer
    (d) a chelator,
    (e) a bulking agent/tonicity adjuster, and
    (f) a buffer.

2. The formulation of claim 1 having a pH from 6.0 to 8.0.

3. The formulation of claim 1, wherein said buffer is selected from the group consisting of phosphoric acid, phosphate, citric acid, citrate, sulfosalicylate, acetic acid, acetate, methyl boronic acid, boronate, disodium succinate hexahydrate, one or more amino acids, lactic acid, lactate, maleic acid, maleate, potassium chloride, benzoic acid, sodium benzoate, carbonic acid, carbonate, bicarbonate, boric acid, borate, sodium chloride, succinic acid, succinate, tartaric acid, tartrate, tris-(hydroxymethyl)aminomethane, and biological buffers.

4. The formulation of claim 1, wherein said buffer is a phosphate buffer.

5. The formulation of claim 4, wherein said buffer is dibasic potassium phosphate.

6. The formulation of claim 1, wherein said surfactant/solubilizer is selected from the group consisting of anionic surfactants, pluronics, poloxamers, SDS, Triton-100, polysorbates, propylene glycol, PEG and similar compounds, Brij58 9poly(oxyethylene)20 cetyl ether, cremophor EL, cetyl trimethylammonium bromide (CTAB), dimethylacetamide (DMA), NP 40 (Nonidet P-40), and N-methyl-2-pyrrolidone (Pharmasolve), and amino acids.

7. The formulation of claim 1, wherein said surfactant is a nonionic surfactant.

8. The formulation of claim 7, wherein said nonionic surfactant is a polysorbate.

9. The formulation of claim 7, wherein said nonionic surfactant is polysorbate 20 or polysorbate 80.

10. The formulation of claim 1, wherein said stabilizer is selected from the group consisting of antioxidants and amino acids.

11. The formulation of claim 10, wherein said stabilizer is an antioxidant.

12. The formulation of claim 11, wherein said stabilizer is sodium metabisulfite.

13. The formulation of claim 1, wherein said formulation comprises a plurality of stabilizers.

14. The formulation of claim 13, wherein said stabilizers comprise L-arginine monohydrochloride, L-methionine, L-lysine monohydrochloride, and sodium metabisulfite.

15. The formulation of claim 1, wherein said bulking agent/tonicity adjuster is selected from the group consisting of mannitol, amino acids, lactose, potassium chloride, sodium chloride, maltose, sucrose, PEG's, trehalose, raffinose, dextrose, cyclodextrins, dextran, galacturonic acid, Ficoll, and polyvinylpyrrolidone (PVP).

16. The formulation of claim 15, wherein said bulking agent/tonicity adjuster is D-mannitol.

17. The formulation of claim 1, wherein said chelator is pentetic acid (DTPA).

18. The formulation of claim 17, wherein said chelator is pentetic acid, said surfactant is polysorbate 20, said buffer is dibasic potassium phosphate, and said bulking agent/tonicity adjuster is D-mannitol.

19. The formulation of claim 1, wherein said formulation is suitable for parenteral administration.

20. A stabilized, physiologically acceptable formulation of sincalide comprising:
    (a) about 0.0008–0.0012 mg/mL sincalide,
    (b) about 20 to 50 mg/mL mannitol,
    (c) about 2 to 7 mg/mL arginine,
    (d) about 0.2 to 1 mg/mL methionine,
    (e) about 2 to 30 mg/mL lysine,
    (f) about 0.002 to 0.012 mg/mL sodium metabisulfite,
    (g) about 0.000001 to 0.003 mg/mL polysorbate 20,
    (h) about 0.1 to 3 mg/mL pentetic acid (DTPA), and
    (i) about 1.1 to 1.8 mg/mL dibasic potassium phosphate.

21. A method for making a stabilized formulation of sincalide, said method comprising the step of mixing: (a) at least one stabilizer, (b) a surfactant/solubilizer, (c) a chelator, (d) a bulking agent/tonicity adjuster, (e) a buffer (f) an aqueous solution, and (g) sincalide.

22. The method of claim 21, wherein said formulation has a pH from 6.0 to 8.0.

23. The method of claim 21, wherein said buffer is selected from the group consisting of phosphoric acid, phosphate, citric acid, citrate, sulfosalicylate, acetic acid, acetate, methyl boronic acid, boronate, disodium succinate hexahydrate, one or more amino acids, lactic acid, lactate, maleic acid, maleate, potassium chloride, benzoic acid, sodium benzoate, carbonic acid, carbonate, bicarbonate, boric acid, borate, sodium chloride, succinic acid, succinate, tartaric acid, taitrate, tris-(hydroxymethyl)aminomethane, and biological buffers.

24. The method of claim 21, wherein said buffer is a phosphate buffer.

25. The method of claim 24, wherein said buffer is dibasic potassium phosphate.

26. The method of claim 21, wherein said surfactant/solubilizer is selected from the group consisting of anionic surfactants, pluronics, poloxamers, SDS, Triton-100, polysorbates, propylene glycol, PEG and similar compounds, Brij58 9poly(oxyethylene)20 cetyl ether, cremophor EL, cetyl trimethylammonium bromide (CTAB), dimethylacetamide (DMA), NP 40 (Nonidet P-40), and N-methyl-2-pyrrolidone (Pharmasolve), and amino acids.

27. The method of claim 21, wherein said surfactant is a nonionic surfactant.

28. The method of claim 27, wherein said nonionic surfactant is a polysorbate.

29. The method of claim 28, wherein said nonionic surfactant is polysorbate 20 or polysorbate 80.

30. The method of claim 21, wherein said stabilizer is selected from the group consisting of antioxidants and amino acids.

31. The method of claim 30, wherein said stabilizer is an antioxidant.

32. The method of claim 30, wherein said stabilizer is sodium metabisulfite.

33. The method of claim 21, wherein said method further comprises mixing a plurality of stabilizers.

34. The method of claim 33, wherein said stabilizers comprise L-arginine monohydrochloride, L-methionine, L-lysine monohydrochloride, and sodium metabisulfite.

35. The method of claim 21, wherein said bulking agent/tonicity adjuster is selected from the group consisting of mannitol, amino acids, lactose, potassium chloride, sodium chloride, maltose, sucrose, PEG's, trehalose, raffinose, dextrose, cyclodextrins, dextran, galacturonic acid, Ficoll, and polyvinylpyrrolidone (PVP).

36. The method of claim 35, wherein said bulking agent/tonicity adjuster is D-Mannitol.

37. The method of claim 21, wherein said chelator is pentetic acid (DTPA).

38. The method of claim 37, wherein said chelator is pentetic acid, said surfactant is polysorbate 20, said buffer is dibasic potassium phosphate, and said bulking agent/tonicity adjuster is D-mannitol.

39. The method of claim 21, wherein said formulation comprises about 0.0008 to 0.0012 mg/mL sincalide; about 20 to 50 mg/mL mannitol, about 2 to 7 mg/mL arginine; about 0.2 to 1 mg/mL methionine; about 2 to 30 mg/mL lysine; about 0.002 to 0.012 mg/mL sodium metabisulfite; about 0.000001 to 0.003 mg/mL polysorbate 20, about 0.1 to 3.0 mg/mL pentetic acid (DTPA); and about 1.1 to 1.8 mg/mL dibasic potassium phosphate.

40. A kit, comprising:
(i) a powder mixture comprising
  (a) sincalide,
  (b) at least one stabilizer,
  (c) a surfactant,
  (d) a chelator,
  (e) a bulking agent/tonicity adjuster, and
  (f) a buffer;
(ii) a container to hold said powder mixture; and
(iii) optionally, a physiologically acceptable fluid.

41. The kit of claim 40, wherein said buffer is selected from the group consisting of phosphoric acid, phosphate, citric acid, citrate, sulfosalicylate, acetic acid, acetate, methyl boronic acid, boronate, disodium succinate hexahydrate, one or more amino acids, lactic acid, lactate, maleic acid, maleate, potassium chloride, benzoic acid, sodium benzoate, carbonic acid, carbonate, bicarbonate, boric acid, borate, sodium chloride, succinic acid, succinate, tartaric acid, tartrate, tris-(hydroxymethyl)aminomethane, and biological buffers.

42. The kit of claim 40, wherein said buffer is a phosphate buffer.

43. The kit of claim 40, wherein said buffer is dibasic potassium phosphate.

44. The kit of claim 40, wherein said surfactant is selected from the group consisting of anionic surfactants, pluronics, poloxamers, SDS, Triton-100, polysorbates, propylene glycol, PEG and similar compounds, Brij58 9poly(oxyethylene)20 cetyl ether, cremophor EL, cetyl trimethylammonium bromide (CTAB), dimethylacetamide (DMA), NP 40 (Nonidet P-40), and N-methyl-2-pyrrolidone (Pharmasolve), and amino acids.

45. The kit of claim 40, wherein said surfactant is a nonionic surfactant.

46. The kit of claim 45, wherein said nonionic surfactant is a polysorbate.

47. The kit of claim 46, wherein said nonionic surfactant is polysorbate 20 or polysorbate 80.

48. The kit of claim 40, wherein said stabilizer is selected from the group consisting of antioxidants and amino acids.

49. The kit of claim 48, wherein said stabilizer is an antioxidant.

50. The kit of claim 49, wherein said stabilizer is sodium metabisulfite.

51. The kit of claim 40, wherein said powder mixture comprises a plurality of stabilizers.

52. The kit of claim 51, wherein said stabilizers comprise L-arginine monohydrochloride, L-methionine, L-lysine monohydrochloride, and sodium metabisulfite.

53. The kit of claim 40, wherein said bulking agent/tonicity adjuster is selected from the group consisting of mannitol, amino acids, lactose, potassium chloride, sodium chloride, maltose, sucrose, PEG's, trehalose, raffinose, dextrose, cyclodextrins, dextran, galacturonic acid, Ficoll, and polyvinylpyrrolidone (PVP).

54. The kit of claim 40, wherein said chelator is pentetic acid (DTPA).

55. The kit of claim 40, wherein said container is a vial.

56. A method for treating or preventing a medical condition associated with total parenteral nutrition (TPN), said method comprising administering to a patient receiving TPN an effective amount of a sincalide formulation, said formulation comprising: (a) sincalide, (b) at least one stabilizer, (c) a surfactant, (d) a chelator, (e) a bulking agent/tonicity adjuster, and (f) a buffer.

57. The method of claim 56, wherein said medical condition is TPN-associated cholestatis.

58. The method of claim 56, wherein said formulation is administered by injection.

59. The method of claim 56, wherein said formulation has a pH from 6.0 to 8.0.

60. The method of claim 56, wherein said buffer is selected from the group consisting of phosphoric acid, phosphate, citric acid, citrate, sulfosalicylate, acetic acid, acetate, methyl boronic acid, boronate, disodium succinate hexahydrate, one or more amino acids, lactic acid, lactate, maleic acid, maleate, potassium chloride, benzoic acid, sodium benzoate, carbonic acid, carbonate, bicarbonate, boric acid, borate, sodium chloride, succinic acid, succinate, tartaric acid, tartrate, tris-(hydroxymethyl)aminomethane, and biological buffers.

61. The method of claim 56, wherein said buffer is a phosphate buffer.

62. The method of claim 61, wherein said buffer is dibasic potassium phosphate.

63. The method of claim 56, wherein said surfactant is selected from the group consisting of anionic-surfactants, pluronics, poloxamers, SDS, Triton-100, polysorbates, propylene glycol, PEG and similar compounds, Brij58 9poly(oxyethylene)20 cetyl ether, cremophor EL, cetyl trimethylammonium bromide (CTAB), dimethylacetamide (DMA), NP 40 (Nonidet P-40), and N-methyl-2-pyrrolidone (Pharmasolve),and amino acids.

64. The method of claim 56, wherein said surfactant is a nonionic surfactant.

65. The method of claim 64, wherein said nonionic surfactant is a polysorbate.

66. The method of claim 65, wherein said nonionic surfactant is polysorbate 20 or polysorbate 80.

67. The method of claim 56, wherein said stabilizer is selected from the group consisting of antioxidants and amino acids.

68. The method of claim 67, wherein said stabilizer is an antioxidant.

69. The method of claim 68, wherein said stabilizer is sodium metabisulfite.

70. The method of claim 56, wherein said method comprises mixing a plurality of stabilizers.

71. The method of claim 69, wherein said stabilizers comprise L-arginine monohydrochloride, L-methionine, L-lysine monohydrochloride, and sodium metabisulfite.

72. The method of claim 56, wherein said bulking agent/tonicity adjuster is selected from the group consisting of mannitol, amino acids, lactose, potassium chloride, sodium chloride, maltose, sucrose, PEG's, trehalose, raffinose, dextrose, cyclodextrins, dextran, galacturonic acid, Ficoll, and polyvinylpyrrolidone (PVP).

73. The method of claim 72, wherein said bulking agent/tonicity adjuster is D-mannitol.

74. The method of claim 56 wherein said chelator is pentetic acid (DTPA).

75. The method of claim 74 wherein said chelator is pentetic acid, said surfactant is polysorbate 20, said buffer is dibasic potassium phosphate, and said bulking agent/tonicity adjuster is D-mannitol.

76. The method of claim 56, wherein said formulation comprises about 0.0008 to 0.0012 mg/mL sincalide; about 20 to 50 mg/mL D-mannitol, about 2 to 7 mg/mL L-arginine; about 0.2 to 1 mg/mL L-methionine; about 2 to 30 mg/mL L-lysine; about 0.002 to 0.012 mg/mL sodium metabisulfite; about 0.000001 to 0.003 mg/mL polysorbate 20, about 0.1 to 3 mg/mL pentetic acid (DTPA); and about 1.1 to 1.8 mg/mL dibasic potassium phosphate.

77. A method for imaging the hepatobiliary system of a subject, said method comprising:
(a) administering a hepatobiliary imaging agent to said subject;
(b) before or after step (a), administering to a subject a sincalide formulation comprising: (i) sincalide, (ii) at least one stabilizer, (iii) a surfactant, (iv) a chelator, (v) a bulking agent/tonicity adjuster, and (vi) a buffer; and
(c) detecting said imaging agent in said subject with a detection device.

78. The method of claim 77, wherein said sincalide formulation is administered by injection.

79. The method of claim 77, wherein said sincalide formulation is administered to said subject before administration of said hepatobiliary imaging agent.

80. The method of claim 77, wherein said sincalide formulation is administered to said subject after administration of said hepatobiliary imagining agent.

81. The method of claim 77, wherein said hepatobiliary imaging agent is a $^{99m}$Tc-IDA (Iminodiacetic acid) analog.

82. The method of claim 77, wherein said hepatobiliary imaging agent is $^{99m}$Tc-mebrofenin.

83. The method of claim 77, wherein said method further comprises, after administration of said sincalide formulation, measuring said the gallbladder ejection fraction (GBEF) of said subject.

84. The method of claim 77, wherein said detection device scans the body of said subject for radioactivity.

85. The method of claim 84, wherein said detection device is a gamma camera.

86. The method of claim 77, wherein said formulation has a pH from 6.0 to 8.0.

87. The method of claim 77, wherein said buffer is selected from the group consisting of phosphoric acid, phosphate, citric acid, citrate, sulfosalicylate, acetic acid, acetate, methyl boronic acid, boronate, disodium succinate hexahydrate, one or more amino acids, lactic acid, lactate, maleic acid, maleate, potassium chloride, benzoic acid, sodium benzoate, carbonic acid, carbonate, bicarbonate, boric acid, borate, sodium chloride, succinic acid, succinate, tartaric acid, tartrate, tris-(hydroxymethyl)aminomethane, and biological buffers.

88. The method of claim 77, wherein said buffer is a phosphate buffer.

89. The method of claim 88, wherein said buffer is dibasic potassium phosphate.

90. The method of claim 77, wherein said surfactant is selected from the group consisting of anionic surfactants, pluronics, poloxamers, SDS, Triton-100, polysorbates, propylene glycol, PEG and similar compounds, Brij58 9poly(oxyethylene)20 cetyl ether, cremophor EL, cetyl trimethylammonium bromide (CTAB), dimethylacetamide (DMA), NP 40 (Nonidet P-40), and N-methyl-2-pyrrolidone (Pharmasolve) and amino acids.

91. The method of claim 77, wherein said surfactant is a nonionic surfactant.

92. The method of claim 91, wherein said nonionic surfactant is a polysorbate.

93. The method of claim 92, wherein said nonionic surfactant is polysorbate 20 or polysorbate 80.

94. The method of claim 77, wherein said stabilizer is selected from the group consisting of antioxidants and amino acids.

95. The method of claim 94, wherein said stabilizer is an antioxidant.

96. The method of claim 95, wherein said stabilizer is sodium metabisulfite.

97. The method of claim 77, wherein said method comprises mixing a plurality of stabilizers.

98. The method of claim 97, wherein said stabilizers comprise L-arginine monohydrochloride, L-methionine, L-lysine monohydrochloride, and sodium metabisulfite.

99. The method of claim 77, wherein said bulking agent/tonicity adjuster is selected from the group consisting of mannitol, amino acids, lactose, potassium chloride, sodium chloride, maltose, sucrose, PEG's, trehalose, raffinose, dextrose, cyclodextrins, dextran, galacturonic acid, Ficoll, and polyvinylpyrrolidone (PVP).

100. The method of claim 77, wherein said bulking agent/tonicity adjuster is D-mannitol.

101. The method of claim 77, wherein said chelator is pentetic acid (DTPA).

102. The method of claim 101, wherein said chelator is pentetic acid, said surfactant is polysorbate 20, said buffer is dibasic potassium phosphate, and said bulking agent/tonicity adjuster is D-mannitol.

103. The method of claim 77, wherein said formulation comprises about 0.0008 to 0.0012 mg/mL sincalide; about 20 to 50 mg/mL D-mannitol, about 2 to 7 mg/mL L-arginine; about 0.2 to 1 mg/mL L-methionine; about 2 to 30 mg/mL L-lysine; about,0.002 to 0.012 mg/mL Sodium metabisulfite; about 0.000001 to 0.003 mg/mL polysorbate 20; about 0.1 to 3 mg/mL pentetic acid (DTPA); and about 1.1 to 1.8 mg/mL dibasic potassium phosphate.

104. A method for imaging the hepatobiliary system of a subject, said method comprising:
- a) administering to a subject a sincalide formulation comprising: (i) sincalide, (ii) at least one stabilizer, (iii) a surfactant, (iv) a chelator, (v) a bulking agent/tonicity adjuster, and (vi) a buffer; and
- b) scanning the subject using a diagnostic imaging modality.

105. The method of claim 104 wherein said imaging modality is selected from the group consisting of magnetic resonance imaging, scintigraphic imaging and ultrasound imaging.

106. A stabilized, physiologically acceptable formulation of sincalide comprising:
- (a) about 0.001 mg/mL sincalide;
- (b) about 34 mg/mL D-mannitol;
- (c) about 6 mg/mL L-arginine;
- (d) about 0.8 mg/mL L-methionine;
- (e) about 3 mg/mL L-lysine;
- (f) about 0.008 mg/mL sodium metabisulfite;
- (g) less than about 0.01 mg/mL polysorbate 20;
- (h) about 0.4 mg/mL pentetic acid; and
- (i) about 1.8 mg/mL dibasic potassium phosphate.

107. The kit of claim 40 comprising:
- a) about 0.005 mg sincalide;
- b) about 100 to 250 mg mannitol;
- c) about 0.000005 to 0.015 mg polysorbate 20;
- d) about 2 mg pentetic acid (DTPA);
- e) about 0.01 to 0.06 mg sodium metabisulfite;
- f) about 5.4 to 12 mg potassium phosphate (dibasic);
- g) about 1 to 5 mg methionine;
- h) about 10 to 60 mg lysine; and
- i) about 10 to 35 mg arginine.

108. A kit comprising:
- a) about 0.005 mg sincalide;
- b) about 170 mg D-mannitol;
- c) less than about 0.01 mg polysorbate 20;
- d) about 2 mg DTPA;
- e) about 0.04 mg sodium metabisulfite;
- f) about 9 mg potassium phosphate (dibasic);
- g) about 4 mg L-methionine;
- h) about 15 mg L-lysine monohydrochloride; and
- i) about 30 mg L-arginine monohydrochloride.

* * * * *